(12) United States Patent
Wang et al.

(10) Patent No.: US 7,043,990 B2
(45) Date of Patent: May 16, 2006

(54) SYSTEM FOR AND METHOD OF PERFORMING EVALUATION TECHNIQUES ON A LOG OR ROUND TIMBER

(75) Inventors: Xiping Wang, Madison, WI (US);
Robert J. Ross, Madison, WI (US);
James A. Mattson, Laurium, MI (US);
John Erickson, Madison, WI (US);
John W. Forsman, Hancock, MI (US);
Earl A. Geske, Cross Plains, WI (US);
Michael A. Wehr, Kewadin, MI (US)

(73) Assignees: Board of Control of Michigan Technological University, Houghton, MI (US); The United States of America as represented by the Secretary of Agriculture, Washington, DC (US)

( * ) Notice: Subject to any disclaimer, the term of this patent is extended or adjusted under 35 U.S.C. 154(b) by 266 days.

(21) Appl. No.: 10/470,145

(22) PCT Filed: Jan. 30, 2002

(86) PCT No.: PCT/US02/02690

§ 371 (c)(1),
(2), (4) Date: Jul. 24, 2003

(87) PCT Pub. No.: WO02/060662

PCT Pub. Date: Aug. 8, 2002

(65) Prior Publication Data
US 2004/0083076 A1 Apr. 29, 2004

Related U.S. Application Data

(60) Provisional application No. 60/265,252, filed on Jan. 31, 2001.

(51) Int. Cl.
*G01N 33/46* (2006.01)
*G01N 3/30* (2006.01)

(52) U.S. Cl. .............................. 73/597; 73/602; 702/56
(58) Field of Classification Search ............... 73/12.01, 73/12.09, 12.12, 573, 579, 580, 581, 582, 73/583, 602; 702/35, 36, 39, 56, 81, 82
See application file for complete search history.

(56) References Cited

U.S. PATENT DOCUMENTS 3,554,249 A * 1/1971 Arnelo et al. ............... 144/357

(Continued)

FOREIGN PATENT DOCUMENTS

DE 4435975 * 4/1995

(Continued)

OTHER PUBLICATIONS

Jayne, B.A. Vibrational properties of wood as indices of quality. Nov. 1959. Forest Prod. J. 9(11): 413-416.

(Continued)

*Primary Examiner*—Hezron Williams
*Assistant Examiner*—Rose M. Miller
(74) *Attorney, Agent, or Firm*—Michael Best & Friedrich LLP

(57) ABSTRACT

A system for and method of evaluating a log. The system includes an analysis module having at least one input terminal connectable to the at least one input device. The at least one input terminal is operable to receive at least one signal representing at least one measured property of the log and at least one determined parameter of the log determined in response to an energy being applied to the log. The analysis module further includes a processor coupled to the at least one input terminal. The processor determines a predictive modulus of elasticity (MOE) of the log based at least in part on the at least one measured property and the at least one sensed parameter. The analysis module also includes an output terminal coupled to the processor and connectable to an output device. The output terminal transmits a third signal representing the predictive MOE.

33 Claims, 18 Drawing Sheets

U.S. PATENT DOCUMENTS

| | | | |
|---|---|---|---|
| 4,805,679 A | * | 2/1989 | Czinner ...................... 144/357 |
| 4,838,085 A | | 6/1989 | Pellerin et al. |
| 4,852,029 A | * | 7/1989 | Pope et al. ................... 702/41 |
| 5,024,091 A | | 6/1991 | Pellerin et al. |
| 5,060,516 A | | 10/1991 | Lau et al. |
| 5,307,679 A | | 5/1994 | Ross |
| 5,396,799 A | | 3/1995 | Ross et al. |
| 6,026,689 A | | 2/2000 | Snyder et al. |
| 6,029,522 A | | 2/2000 | Schafer et al. |

FOREIGN PATENT DOCUMENTS

| | | | |
|---|---|---|---|
| EP | 0 326 284 | | 8/1989 |
| GB | 1244699 | * | 9/1971 |
| JP | 11064306 A | * | 3/1999 |
| JP | 2000105228 A | * | 4/2000 |
| NZ | 337015/337186 | | 7/2002 |
| WO | WO 8810415 A | * | 12/1988 |
| WO | WO 9801737 A | * | 1/1998 |
| WO | WO 9944059 A | * | 9/1999 |
| WO | WO 00/36413 | | 6/2000 |

OTHER PUBLICATIONS

Kaiserlik, J.H., R.F. Pellerin. Stress wave attenuation as an indicator of lumber strength. Jun. 1977. Forest Prod. J. 27(6): 39-43.

Pellerin, R.F. A vibrational approach to nondestructive testing of structural lumber. Mar. 1965. Forest Prod. J. 14(3): 93-101.

Ross, R.J., E.A. Geske, G.L. Larson, J.F. Murphy. Transverse vibration nondestructive testing using a personal computer. Aug. 1991. Madison, WI: U.S. Department of Agriculture, Forest Service, Forest Products Laboratory. Res. Pap. FPL-RP-502. 17 p.

Ross, R.J., R.F. Pellerin. Nondestructive testing for assessing wood members in structures: A review. Rev. May 1994. Madison, WI: U.S. Department of Agriculture, Forest Service, Forest Products Laboratory. Gen. Tech. Rep. FPL-GTR-70. 40 p.

Ross, R.J., R.C. DeGroot, W.J. Nelson. Technique for non-destructive evaluation of biologically degraded wood. Sep. 1994. Experimental Techniques. 18(5): 29-32.

Ross, R.J., K.A. McDonald, D.W. Green, K.C. Schad. Relationship between log and lumber modulus of elasticity. Feb. 1996. Forest Prod. J. 47(2): 89-92.

Ross, R.J., S.W. Willits, W.V. Segen, T. Black, B.K. Brashaw, R.F. Pellerin. A stress wave based approach to NDE of logs for assessing potential vencer quality. Part 1. Small-diameter ponderosa pine. Feb. 1999. Forest Prod. J. 49(11/12): 60-62.

Schad, K.C., D.E. Kretschmann, K. McDonald, R. Ross, D.W. Green. Stress wave techniques for determining quality of dimensional lumber from switch ties. Aug. 1995. Madison, WI: U.S. Department of Agriculture, Forest Service, Forest Products Laboratory. Res. Note FPL-RN-0265. 12 p.

Wang, X., R.J. Ross, J.R. Erickson, J.W. Forsman, G.D. McGinnis, R.C. Degroot. Nondestructive methods of evaluating quality of wood in preservative-treated piles. Mar. 2000. Madison, WI: U.S. Department of Agriculture, Forest Service, Forest Products Laboratory. Res. Note FPL-RN-0274. 9 p.

Wang, X. Stress wave-based nondestructive evaluation (NDE) methods for wood quality of standing trees, A Dissertation. Aug. 1999. Michigan Technological University, Houghton, Michigan. 187 p.

Wolfe, R. Research challenges for structural use of small-diameter round timbers. Feb. 2000. Forest Prod. J.50(2): 21-29.

Xiping Wang et al., United States Department of Agriculture, Several Nondestructive Evaluation Techniques for Assessing Stiffness and MOE of Small-Diameter Logs; May 2001.

Robert J. Ross et al., 12th International Symposium on Nondestructive Testing Wood, Comparison of Several Nondestructive Techniques for Assessing Stiffness and MOE of Small-Diameter Logs, Sep. 13-15, 2000, pp. 155-163.

* cited by examiner

TABLE 1. PHYSICAL CHARACTERISTICS OF RED PINE AND JACK PINE LOGS[A]

| SPECIES AND LOG GROUP | NUMBER OF LOGS | DBH OF TREES (IN) | | DIAMETER OF BUTT LOGS (IN) | | DENSITY (LB/FT³) | | MOISTURE CONTENT (%) | |
|---|---|---|---|---|---|---|---|---|---|
| | | AVERAGE | MINIMUM-MAXIMUM | AVERAGE | MINIMUM-MAXIMUM | AVERAGE | MINIMUM-MAXIMUM | AVERAGE | MINIMUM-MAXIMUM |
| RED PINE | | | | | | | | | |
| 22[B] | 10 | 9.82 | 8.50-10.35 | 9.16 | 7.90-10.13 | 53.3 | 49.7-56.0 | 113.6 | 114.1-144.6 |
| 32 | 10 | 9.87 | 8.12-11.10 | 9.16 | 7.63-10.16 | 53.8 | 52.3-56.7 | 121.1 | 114.5-140.4 |
| 42 | 10 | 8.67 | 7.88-9.02 | 7.99 | 7.37-8.31 | 54.2 | 51.9-56.5 | 115.3 | 88.2-132.6 |
| 62 | 10 | 7.23 | 5.48-8.70 | 6.79 | 5.30-8.16 | 50.9 | 48.0-52.8 | 109 | 121.7-134.5 |
| 82 | 10 | 6.72 | 4.70-7.86 | 6.24 | 4.40-7.42 | 52.7 | 49.4-54.4 | 116.7 | 116.7-145.2 |
| JACK PINE | | | | | | | | | |
| MERCHANTABLE LIVE | 30 | 9.4 | 7.4-11.0 | 8.59 | 6.83-9.90 | 47.04 | 42.18-53.73 | 65 | 50.9-107.2 |
| SUSPECT | 29 | 9.4 | 6.4-12.0 | 8.47 | 6.14-10.99 | 42.26 | 29.01-51.38 | 54.1 | 40.2-74.3 |
| MERCHANTABLE DEAD | 32 | 7.9 | 5.0-12.2 | 7.11 | 4.67-10.56 | 34.91 | 28.66-43.34 | 36.8 | 21.0-55.7 |
| NONMERCHANTABLE DEAD | 13 | 7.6 | 6.3-9.7 | 6.65 | 5.58-8.50 | 34.58 | 29.46-42.16 | 31.2 | 20.6-38.4 |

[A] 1 IN. = 2.54 MM, 1 LB/FT³ = 16.01 KG/M³
[B] NUMBER OF TREES PER 1/10 ACRE

Fig. 12

TABLE 2. MODULUS OF ELASTICITY (MOE) OF RED PINE AND JACK PINE LOGS[A]

| SPECIES | NUMBER OF LOGS | DYNAMIC MOE (MOE$_{SW}$) | | | DYNAMIC MOE (MOE$_V$) | | | STATIC MOE (MOE$_S$) | | |
|---|---|---|---|---|---|---|---|---|---|---|
| | | MEAN | SD | MINIMUM-MAXIMUM | MEAN | SD | MINIMUM-MAXIMUM | MEAN | SD | MINIMUM-MAXIMUM |
| RED PINE | 50 | 0.95 | 0.11 | 0.76-1.22 | 0.85 | 0.164 | 0.58-1.22 | 0.8 | 0.187 | 0.45-1.21 |
| JACK PINE | 109 | 1.11 | 0.23 | 0.47-1.84 | 0.87 | 0.246 | 0.25-1.47 | 0.81 | 0.235 | 0.17-1.48 |

[A]MOE$_{SW}$ - DYNAMIC MODULUS OF ELASTICITY DETERMINED BY STRESS WAVE TECHNIQUE.
MOE$_V$ - DYNAMIC MODULUS OF ELASTICITY DETERMINED BY TRANSVERSE VIBRATION TECHNIQUE.
MOE$_S$ - STATIC MODULUS OF ELASTICITY OF LOG DETERMINED BY GENERAL BENDING.
SD - STANDARD DEVIATION

Fig. 13

TABLE 3. RESULTS OF LINEAR REGRESSION ANALYSES OF VARIOUS MOES OF RED PINE AND JACK PINE LOGS[A]

| SPECIES | MOE Y | MOE X | LINEAR REGRESSION MODEL Y = A + BX | | | | | |
|---|---|---|---|---|---|---|---|---|
| | | | A | B | $R^2$ | R | $S_{YX}$ | F |
| RED PINE | | | | | | | | |
| | $MOE_V$ | $MOE_{SW}$ | -2.7076 | 1.3100 | 0.77 | 0.88 | 0.545 | 162.1 *** |
| | $MOE_S$ | $MOE_{SW}$ | -4.1270 | 1.4740 | 0.75 | 0.87 | 0.653 | 143.1 *** |
| | $MOE_S$ | $MOE_V$ | -0.9947 | 1.1105 | 0.95 | 0.97 | 0.304 | 835 *** |
| JACK PINE | | | | | | | | |
| | $MOE_V$ | $MOE_{SW}$ | -0.2190 | 0.8167 | 0.58 | 0.76 | 1.104 | 142.4 *** |
| | $MOE_S$ | $MOE_{SW}$ | -0.4437 | 0.7883 | 0.60 | 0.77 | 1.032 | 150.9 *** |
| | $MOE_S$ | $MOE_V$ | 0.2929 | 0.8782 | 0.85 | 0.92 | 0.635 | 567.1 *** |
| COMBINED | | | | | | | | |
| | $MOE_V$ | $MOE_{SW}$ | 0.3298 | 0.7748 | 0.55 | 0.74 | 1.036 | 182.9 *** |
| | $MOE_S$ | $MOE_{SW}$ | 0.0611 | 0.7555 | 0.53 | 0.73 | 1.040 | 172.4 *** |
| | $MOE_S$ | $MOE_V$ | 0.0839 | 0.9175 | 0.86 | 0.93 | 0.565 | 946.9 *** |

[A] $MOE_{SW}$ - MODULUS OF ELASTICITY (MOE) OF A LOG DETERMINED BY STRESS WAVE METHOD.
$MOE_V$ - MOE OF A LOG DETERMINED BY TRANSVERSE VIBRATION METHOD.
$MOE_S$ - MOE OF A LOG DETERMINED BY FOUR-POINT STATIC BENDING.
$R^2$ - COEFFICIENT OF DETERMINATION
R - CORRELATION COEFFICIENT
$S_{YX}$ - STANDARD ERROR OF ESTIMATE.
*** HIGHLY SIGNIFICANT (0.01 CONFIDENCE LEVEL) BY F-TEST.

Fig. 14

TABLE 4. RESULTS OF REGRESSION ANALYSES RELATING STATIC BENDING MOE TO STRESS WAVE MOE AND D/L[A]

| SPECIES | | | | REGRESSION MODEL $Y = A X_1^B X_2^C$ | | | | | |
|---|---|---|---|---|---|---|---|---|---|
| | Y | $X_1$ | $X_2$ | A | B | C | $R^2$ | R | $S_{YX}$ |
| RED PINE | $MOE_S$ | $MOE_{SW}$ | D/L | 0.0968 | 0.9078 | -0.7326 | 0.91 | 0.953939 | 0.055 |
| JACK PINE | $MOE_S$ | $MOE_{SW}$ | D/L | 1.7826 | 1.1957 | -0.5060 | 0.74 | 0.860233 | 0.120 |

[A]$MOE_{SW}$ - MODULUS OF ELASTICITY (MOE) OF A LOG DETERMINED BY STRESS WAVE METHOD.
$MOE_S$ - MOE OF A LOG DETERMINED BY FOUR-POINT STATIC BENDING.
$R^2$ - COEFFICIENT OF DETERMINATION
R - CORRELATION COEFFICIENT
$S_{YX}$ - STANDARD ERROR OF ESTIMATE.

Fig. 15

TABLE 5. RESULTS OF REGRESSION ANALYSES OF FLEXURAL STIFFNESS (EI) OF LOGS DETERMINED BY DIFFERENT TECHNIQUES[A]

| SPECIES | | | REGRESSION MODEL $Y = A + BX + CX^2$ OR $Y = A + BX$ | | | | | |
|---|---|---|---|---|---|---|---|---|
| | Y | X | A | B | C | $R^2$ | R | $S_{yx}$ |
| COMBINED | $EI_v$ | $EI_{sw}$ | 5.13 | 0.9035 | -0.00049 | 0.97 | 0.98 | 18.03 |
| | $EI_s$ | $EI_{sw}$ | 11.68 | 0.7530 | -0.00028 | 0.94 | 0.97 | 23.37 |
| | $EI_s$ | $EI_v$ | -1.83 | 0.9434 | -- | 0.94 | 0.97 | 22.83 |

[A] $EI_{sw}$ - STIFFNESS OF LOG DETERMINED BY LONGITUDINAL STRESS WAVE TECHNIQUE.
$EI_v$ - STIFFNESS OF LOG DETERMINED BY TRANSVERSE VIBRATION TECHNIQUE.
$EI_s$ - STIFFNESS OF LOG DETERMINED BY FOUR-POINT STATIC BENDING.
$R^2$ - COEFFICIENT OF DETERMINATION
R - CORRELATION COEFFICIENT
$S_{yx}$ - STANDARD ERROR OF ESTIMATE.

Fig. 22

SYSTEM FOR AND METHOD OF PERFORMING EVALUATION TECHNIQUES ON A LOG OR ROUND TIMBER

RELATED APPLICATIONS

This application claims the benefit of U.S. Provisional Application No. 60/265,252, entitled SYSTEM FOR AND METHOD OF PERFORMING NONDESTRUCTIVE EVALUATION TECHNIQUES ON A LOG OR ROUND TIMBER, filed on Jan. 31, 2001.

STATEMENT REGARDING FEDERALLY SPONSORED RESEARCH FOR DEVELOPMENT

This invention was made with United States government support under 99-RJVA-3256 awarded by the United States Department of Agriculture. The government has certain rights in the invention.

BACKGROUND OF THE INVENTION

The invention relates to a system for and method of performing nondestructive evaluation techniques on a log or round timber and, particularly, a system for and method of performing nondestructive evaluation techniques on a log or round timber for assessing the stiffness and modulus of elasticity of the log or round timber.

Many decades of inappropriate management practices, or lack of management altogether, have produced large acreages of forest stands that are overstocked with small-diameter trees of mixed species. These stands are typically low in value, and the harvestable material will not cover the costs of needed management treatments. A specific example is the interior west region of the United States, where 39 million acres of ponderosa pine-type forest have lost ecological integrity due to major changes in vegetative structure and composition. These changes have been caused by control of fire in an ecosystem where historically there were frequent, low-intensity stand maintenance fires. Exclusion of fire has led to the current conditions where these stands are now at high risk of attack by insects, disease, and stand destroying wildfires. Restoration, either mechanical or through prescribed fires, can cost $150-$500 per acre. It is essential to find cost-effective products that can be produced from the materials available in these stands so that needed management operations such as thinning can be implemented to improve the condition of these stands. Economical and value-added uses for these removals can help offset forest management costs, provide economic opportunities for many small, forest-based communities, and avoid future loss caused by catastrophic wildfires. Among the issues of great concern for engineering applications of these removals are the variability and predictability of their strength and stiffness.

SUMMARY OF THE INVENTION

A critical need for addressing this situation is the development of nondestructive technologies for evaluating the potential quality of stems and logs obtained from trees in such ecosystems. Static bending, transverse vibration, and longitudinal stress wave techniques are frequently used to assess the modulus of elasticity (MOE) of lumber. Excellent correlations between MOE values obtained from these techniques have been shown to exist. Even greater correlations exist when using developed models that allow for the prediction of static bending properties.

Accordingly, in one embodiment, the invention provides a method of evaluating a log. The method includes the acts of determining a measured modulus of elasticity (MOE) of the log, measuring a property of the log, and calculating a modified MOE based at least in part on the measured MOE and the measured property.

In another embodiment, the invention provides an analysis module for evaluating a log including at least one input terminal connectable to the at least one input device. The at least one input terminal is operable to receive at least one signal representing at least one measured property of the log and at least one determined parameter of the log determined in response to an energy being applied to the log. The analysis module further includes a processor coupled to the at least one input terminal. The processor determines a predictive modulus of elasticity (MOE) of the log based at least in part on the at least one measured property and the at least one sensed parameter. The analysis module also includes an output terminal coupled to the processor and connectable to an output device. The output terminal is operable to transmit a third signal representing the predictive MOE.

In yet another embodiment, the invention provides a system for evaluating a log. The system includes an input device operable to acquire at least one property of the log and to generate a first signal representing the at least one property. The system also includes a sensor attachable to the log. The sensor is operable to sense a stress wave propagating through the log and to generate a second signal representing at least one parameter of the sensed stress wave. The system further includes an analysis module coupled to the input device. The analysis module is operable to receive the first and second signals, to determine a predictive modulus of elasticity (MOE) based at least in part on the first and second signal, and to generate a third signal representing the modified modulus of elasticity. The system also includes an output device operable to receive the third signal.

In even yet another embodiment, the invention provides a software program for evaluating a log. The software program includes at least one software module stored in a computer readable medium. The software module is executable to receive at least one measured property of the log including a diameter of the log, receive at least one determined parameter of the log determined in response to an energy being applied to the log, calculate a predictive modulus of elasticity (MOE) based at least in part on the diameter and the determined parameter, and output the determined modulus of elasticity.

Other features and advantages of the invention will become apparent by consideration of the detailed description and accompanying drawings.

BRIEF DESCRIPTION OF THE DRAWINGS

FIG. 12 is a table representing the physical characteristics of red pine and jack pine logs.

FIG. 13 is a table representing the MOE of red pine and jack pine logs.

FIG. 14 is a table representing the results of linear regression analyses of various $MOE_S$ of red pine and jack pine logs.

FIG. 15 is a table representing the results of linear regression analyses of various $MOE_S$ of red pine and jack pine logs.

FIG. 24 is a table representing the results of regression analysis of flexural stiffness (EI) of logs determined by different techniques

FIG. 27 is a graph representing the relationships of vibration EI to static EI.

DETAILED DESCRIPTION

Before any embodiments of the invention are explained, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
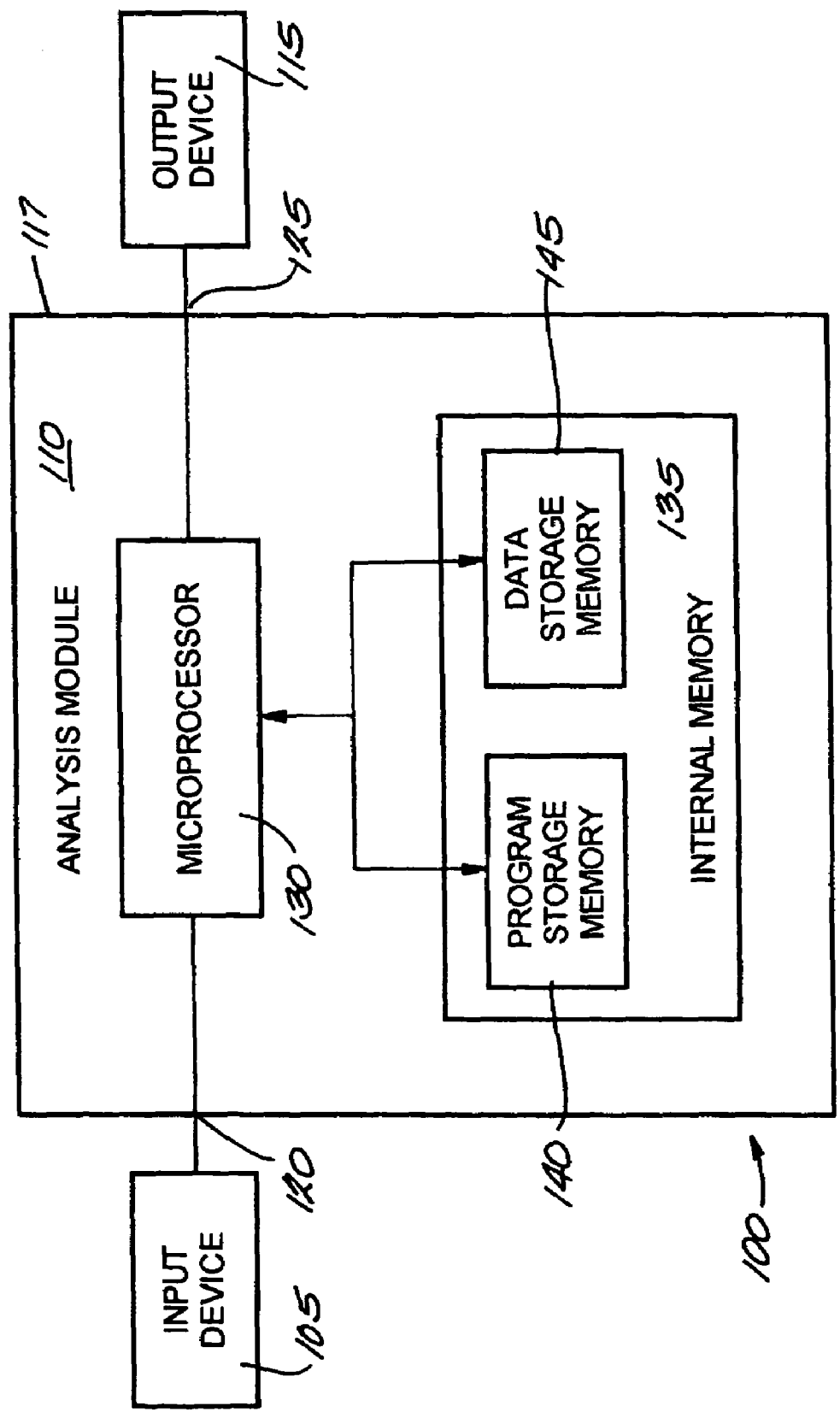
FIG. 1 is a schematic diagram of a system for evaluating a log embodying the invention.

A system for evaluating a log or round timber 100 (collectively referred to herein as a "log") is schematically shown in FIG. 1. The system generally includes one or more input devices 105, an analysis module 110, and one or more output devices 115. The analysis module 110 includes a housing 117 having one or more input terminals 120 and one or more output terminals 125. The terminals 120 and 125 are connectable to the one or more input devices 105 and the one or more output devices 115, respectively. In other embodiments, the analysis module 110 is directly connected to the one or more input devices 105 and the one or more output devices 115. In yet other embodiments, one or more devices of the one or more input devices 105 and/or one or more devices of the one or more output devices 115 are incorporated within the analysis module 110. Even yet other embodiments and arrangements of the one or more input devices 105, the analysis module 110 and the one or more output devices 115 will become apparent based on the description below.

As used herein, the term "connection," and variations thereof (e.g., connect, connected, connecting, etc.), includes direct and indirect connections. The connection, unless specified, may be by mechanical, electrical, chemical, and/or electromagnetic means, or any combination of the foregoing (e.g. electro-mechanical).

In general, the one or more input devices 105 provide input signals to the analysis module 110. The input signals include input or data. For example, in one embodiment, the input signals include data relating to one or more measured physical properties of a log. As used herein, the term "physical properties" refers to a measured characteristic or trait relating to the material log. Example measured properties include a diameter of the log, a radius of the log, a length of the log, a cross-sectional area of the log, a volume of the log, etc.

Another possible input signal includes data or measurements relating to a sensed parameter when a force or energy (e.g., a stress wave, a vibration, a mechanical displacement force, etc.) is applied to the log. For example, the input signal may include information or data resulting from a stress wave (discussed further below) being applied to the log, information or data resulting from a transverse vibration (discussed further below) being applied to the log, or information or data resulting from a force (discussed further below) being applied to the log. For a specific example and in some embodiments, the one or more input signals include data representing an average time between peaks when a stress wave is applied to the log. For another specific example and in other embodiments, the one or more input signals include data representing a modules of elasticity for a stress wave measurement ($MOE_{SW}$). Using the input signals, the analysis module 110 determines a MOE, which may be a predictive or modified MOE, and/or a flexural stiffness for the log. The analysis module 110 then outputs the resulting determination(s) to the one or more output devices.

As shown in FIG. 1, the system 100 includes one or more input devices 105 that provide one or more input signals to the analysis module 110. In one embodiment of the invention, the one or more input devices 105 include one or more operator-controlled input devices for entering data. The one or more operator-controlled input devices allow an operator to control the system 100 and/or to provide data to the analysis module 125. Example operator-controlled input devices include one or more push buttons, one or more trim knobs, a keyboard, a keypad, a touch screen, a pointing device (e.g., a mouse, a trackball), or similar devices. In other embodiments, the one or more input devices 105 include one or more acquisition devices. Example acquisition devices include accelerometer, an oscilloscope, a Metriguard Model 312 Bending Proof Tester, a dial gauge, an electronic recording device for obtaining a load-deflection signal, and similar devices. Other input devices that may be used with the invention include storage devices for providing data (e.g., magnetic storage devices, optical storage devices, etc.), or even a network connection that connects the analysis module to another digital device.

As shown in FIG. 1, the system 100 includes an analysis module 110. The analysis module 110 includes a microprocessor 130, and internal memory 135 having program storage memory 140 and data storage memory 145. The analysis module 110 may include other circuitry (e.g., filters, analog-to-digital converters, drivers, power circuitry, etc.), which are not shown, to implement the invention.

For the embodiment shown, the program storage memory 140 includes one or more software modules having instructions, and the microprocessor 130 retrieves, interprets, and executes the instructions of the one or more software modules to control the system 100. This includes receiving the one or more input signals, determining the MOE and/or flexural stiffness of a log using the one or more input signals, and outputting the calculation(s) to the one or more output devices 115. Different methods of determining the MOE and/or flexural stiffness are discussed below.

In one embodiment of the invention, the analysis module 110 is a standard personal computer. In other embodiments, the analysis module 110 is a hand-held device, a personal data assistant, an Internet appliance or similar device. In yet other embodiments, the analysis module 110 includes any number of processors or controllers constructed with other analog and/or digital logic circuitry having integrated and/or discrete circuit elements.

As shown in FIG. 1, the system 100 includes the one or more output devices 115. Example output devices are a video display, a printer, an external storage device, a second processor connected via a network, and similar devices. The one or more output devices 115 may be incorporated with the one or input devices 105. For example, in one embodiment, the input and output devices 105 and 115 include a touch screen. For another example, the input and output device 105 and 115 include an acquisition device controlled completely or in part by the analysis module 110.

Figure 2:
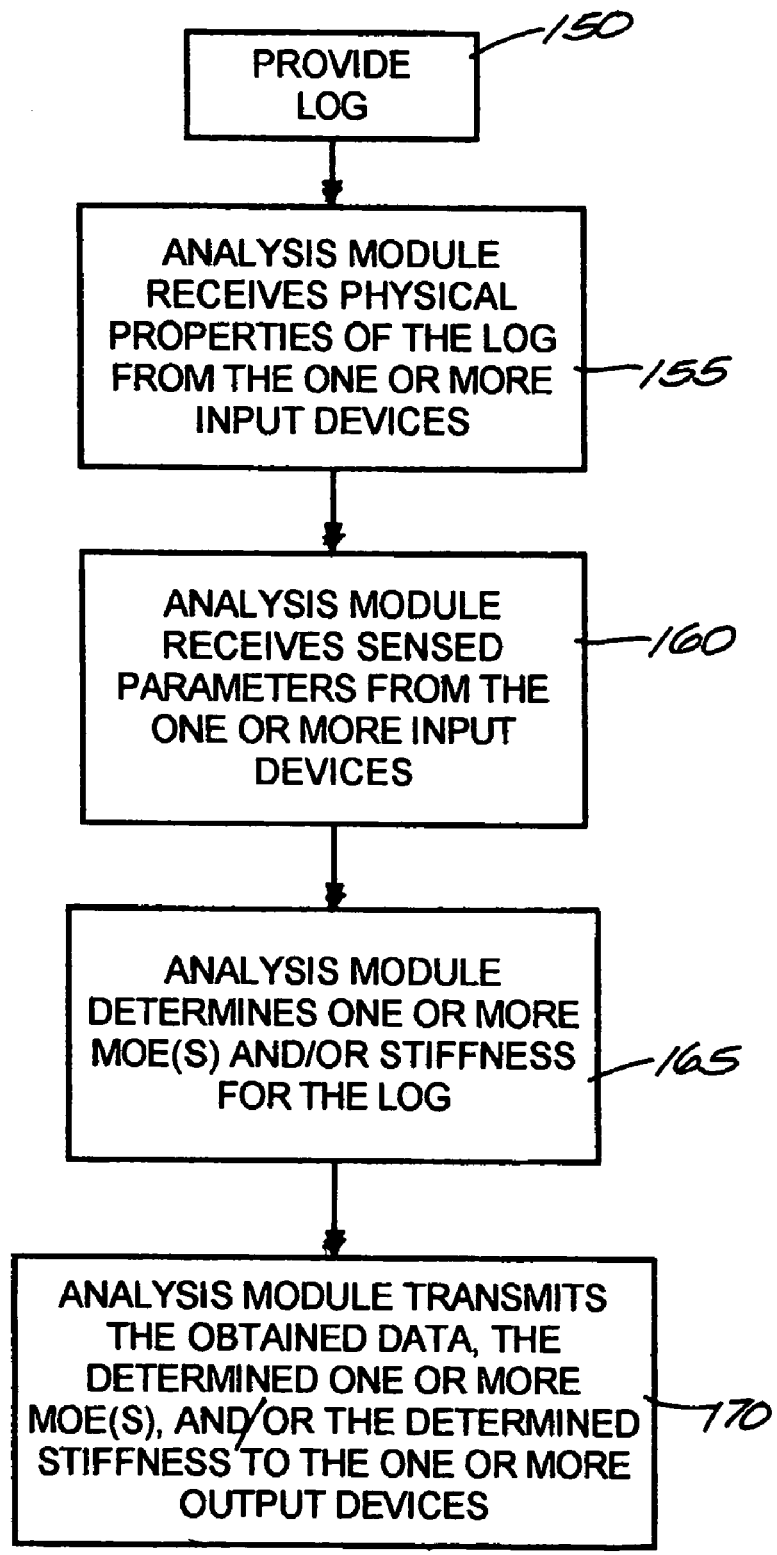
FIG. 2 is a flow chart of a method for evaluating a log embodying the invention.

The components of the system 100 will be further understood by reviewing the operation of the system 100. As schematically shown in FIG. 2, a log is provided for analysis (act 150). At act 155, the analysis module 110 receives the physical properties of the log from the one or more input devices 105. Different methods for receiving the physical properties include: manually entering data using the operator-controlled input device; acquiring the measurements with an acquisition device, and providing an acquisition signal or measured data to the analysis module 110; and providing data via a storage device or network connection.

At act 160, the analysis module 110 receives the sensed parameters from the one or more input devices 105. Different method for providing the sensed parameters include: manually entering data using the operator-controlled input device; acquiring the parameter with an acquisition device, and providing an acquisition signal or measured data to the analysis module 110; and providing data via a storage device or network connection.

At act 165, the analysis module 110 determines one or more modulus of elasticities, and/or flexural stiffness for the log. In some embodiments, the determined MOE is a predictive or modified MOE. Different methods for calculating the MOE and the stiffness are discussed below. At act 170, the analysis module 110 transmits the obtained data, the one or more MOE(s) and/or the flexural stiffness to the one or more output devices 115.

Different methods for determining the MOE and/or stiffness are now discussed.

1. DETERMINING A MOE USING A STATIC-BENDING TECHNIQUE

Figure 3:
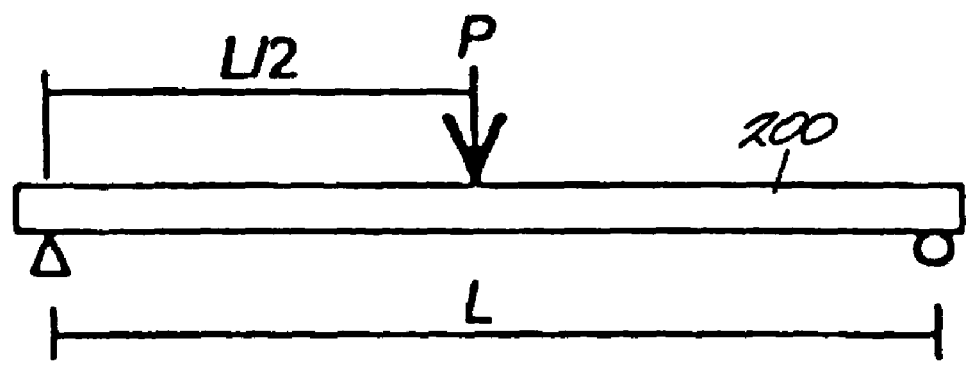
FIG. 3 is a schematic diagram representing a three-point, static-bending technique performed on a log.

Measuring the modulus of elasticity of a log using a static-bending technique involves utilizing the load-deflection relationship of a simply supported beam with different loading patterns. The analysis module 110 determines the static MOE ($MOE_S$) using equations derived from the fundamental mechanics of materials. For example, FIG. 3 schematically shows a standard bending configuration. A load P is applied at the mid-span of the log 200. An acquisition device (e.g., a dial gauge or electronic recording equipment) senses a load-deflection, and transmits a load-deflection signal or measured deflection data to the analysis module 110. Additionally, a length of the log 200 is measured (e.g., by hand or by a second acquisition device) and is provided to analysis module 110. The analysis module 110 then determines a static MOE using data taken from the linear elastic region of the load-deflection curve.

Specifically, the analysis module 110 uses the equation:

$$MOE_S = \frac{PL^3}{48\delta I} \quad (1)$$

where P is the load within the proportional limit, L is the beam span, δ is the deflection at the mid-span within the proportional limit, and I is the beam moment of inertia.

Figure 4:
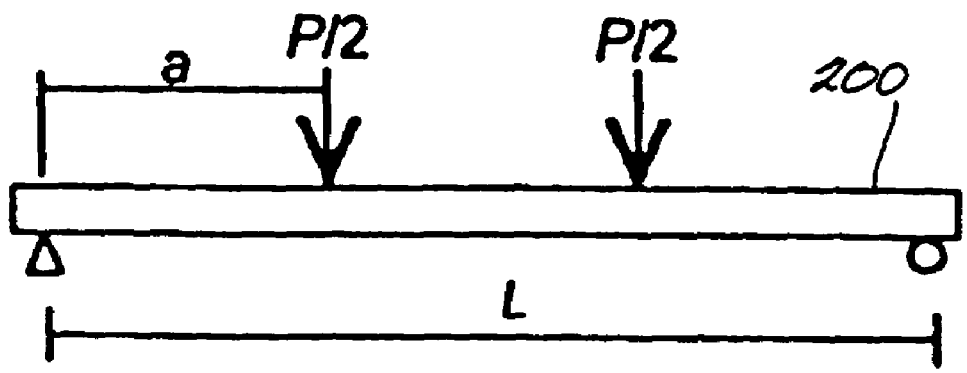
FIG. 4 is a schematic diagram representing a four-point, static-bending technique performed on a log.

For another example of a static-bending technique, FIG. 4 schematically shows a four-point bending configuration. Loads P/2 are equally applied at two points of the log 200. Similar to FIG. 3, the analysis module 110 receives a load deflection signal or measured deflection data, and a length of the log 200. The static MOE for this example is calculated by the following equation:

$$MOE_S = \frac{Pa(3L^2 - 4a^2)}{48\delta I} \quad (2)$$

where P is the load, a is the distance from the end support to the nearest load point, L is the beam span, δ is the mid-span deflection, and I is the beam moment of inertia. A specific embodiment for determining a static MOE is provided below.

2. DETERMINING A MOE USING A TRANSVERSE-VIBRATION TECHNIQUE

Figure 5:
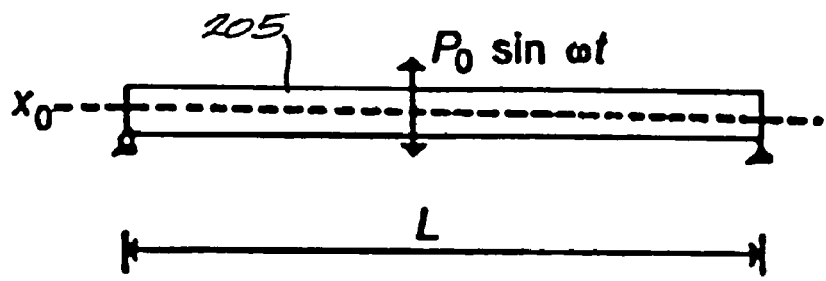
FIG. 5 is a schematic diagram representing a transverse-vibration technique performed on a log.
Figure 6:
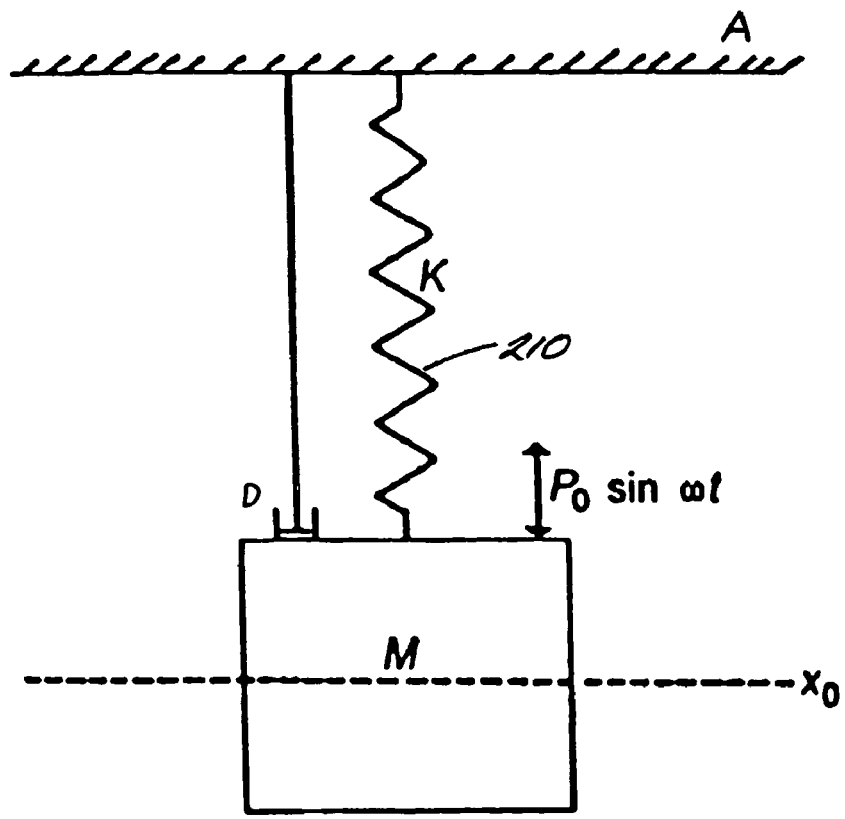
FIG. 6 is a schematic diagram representing an analogy for the transverse-vibration technique shown in FIG. 5.

To illustrate a method of measuring the MOE of a log using a transverse-vibration technique ($MOE_T$), an analogy can be drawn between the behavior of a vibrating log 205 (FIG. 5) and the vibration of a mass M (FIG. 6) that is attached to a weightless spring and internal damping force. As shown in FIG. 6, mass M is supported from a rigid body by a weightless spring 210 whose stiffness is denoted by K. Internal friction or damping is represented by the dashpot D. A forcing function equaling $P_0 \sin \omega t$ or zero is applied for forced and free vibration, respectively. When mass M is set into vibration, its equation of motion can be expressed as follows:

$$M\left(\frac{d_2 x}{dt^2}\right) + D\left(\frac{dx}{dt}\right) + Kx = P_0 \sin \varpi \tau \quad (3)$$

Equation (3) can be solved for either K or D. A solution for K will lead to an expression for a $MOE_T$ of a beam freely supported at two nodal points:

$$MOE_T = \frac{f_r^2 W L^3}{12.65 I g} \quad (4)$$

and for a $MOE_T$ of a beam simply supported at its ends:

$$MOE_T = \frac{f_r^2 W L^3}{2.46 I g}. \quad (5)$$

In Equations (4) and (5), the $MOE_T$ is a dynamic modulus of elasticity (lb/in$^2$ (Pa)), where $f_r$ is the resonant frequency (Hz), W is the beam weight (lb (kg)), L is the beam span (in. (m)), I is the beam moment of inertia (in$^4$ (m$^4$)), and g is the acceleration due to gravity (386 in/s$^2$ (9.8 m/s$^2$)).

Examples of various systems for performing a transverse vibration evaluation are shown in: JAYNE, B. A., Vibrational properties of wood as indices of quality, Forest Prod. J. 9(11), 1959, pp. 413–416; KAISERLIK et al., Stress wave attenuation as an indicator of lumber strength, Forest Prod. J. 27(6), 1977, pp. 39–43; PELLERIN, R. F., A vibrational approach to nondestructive testing of structural lumber, Forest Prod. J. 1 4(3), 1965, pp. 93–101; ROSS et al., Transverse vibration nondestructive testing using a personal computer, Res. Pap. FPL-RP-502 Madison, Wis.:U.S. Department of Agriculture, Forest Service, Forest Products Laboratory, 1991; and ROSS et al., Nondestructive testing for assessing wood members in structures: A review, Gen. Tech. Rep. FPL-GTR-70 (Rev.), Madison, Wis.: U.S. Department of Agriculture, Forest Service, Forest Products Laboratory, 1994, p. 40.; which are all incorporated herein by reference. Additionally, a specific embodiment for determining a $MOE_T$ is provided below.

3. DETERMINING A MOE USING A STRESS-WAVE-PROPAGATION TECHNIQUE.

Figure 7:
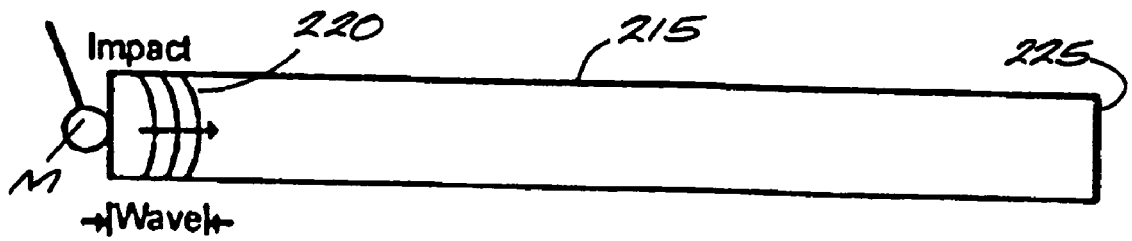
FIG. 7 is a schematic diagram representing a stress-wave measurement technique performed on a log.

To illustrate a method of measuring the MOE of a log using a stress-wave-propagation technique ($MOE_{SW}$), consider application of one-dimensional wave theory to a homogeneous viscoelastic bar 215 (FIG. 7). After a mass M hits the end of the bar 215, a compressive stress wave 220 is generated in the bar 215 and travels from left to right at a speed C. As the wave reaches the free end 225, it is reflected as a tension wave and begins traveling back down the bar 215. Energy is dissipated as the wave travels through the bar 215; therefore, although the speed of the wave remains constant, movement of particles diminishes with each successive passing of the wave. Eventually all particles of the bar 215 come to rest.

Figure 8:
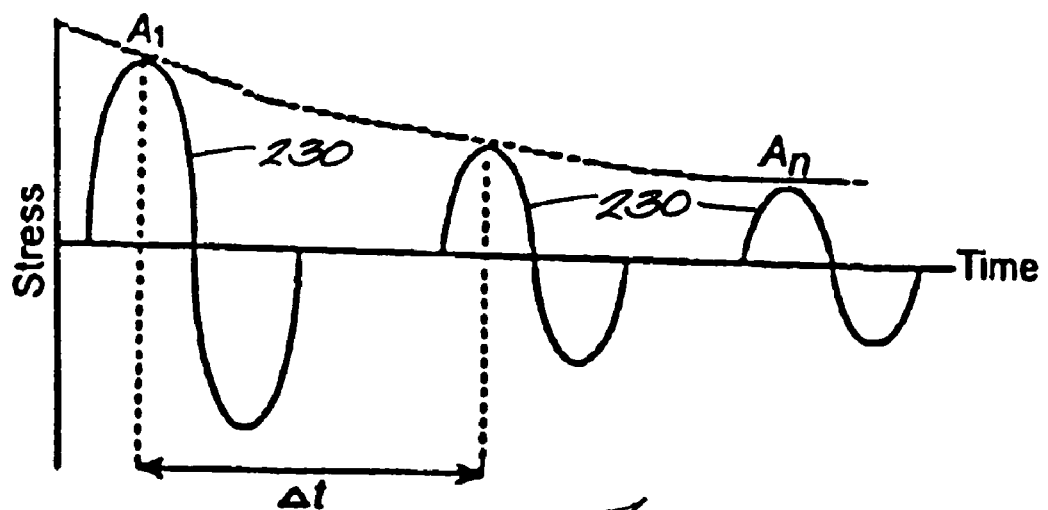
FIG. 8 is a graph representing a theoretical response at the end of the log in response to a propagating stress wave.

Monitoring the movement of a cross section near the end of such a bar in response to a propagating stress wave results in waveforms that include a series of equally spaced pulses 230 (FIG. 8) whose magnitude decreases exponentially with time. The propagation speed C of such a wave can be determined by coupling measurements of the time between pulses At and the length of the bar L by $$C = \frac{2L}{\Delta t} \quad (6)$$

The $MOE_{SW}$ can be computed using C and the mass density of the bar $\rho$:

$$MOE_{SW} = C^2 \rho \quad (7)$$

Although this equation was derived for an idealized one-dimensional case, it has been shown to exist for actual three-dimensional members so long as the length of the wave is large relative to the lateral dimensions of the member (i.e., log).

Examples of various systems for performing a stress-wave evaluation are shown in: ROSS et al., Technique for nondestructive evaluation of biologically degraded wood. Experimental Tech. 18(5), 1994, pp. 29–32; Ross et al., Relationship between log and lumber modulus of elasticity, Forest Prod. J. 47(2), 1996, pp. 89–92; ROSS et al., A stress wave based approach to NDE of logs for assessing potential veneer quality, Part 1. Small-diameter ponderosa pine, Forest Prod. J. 49(1 1/12), 1999, pp. 60–62; SCHAD et al., Stress wave techniques for determining quality of dimensional lumber from switch ties, FPL-RN-0265, USDA Forest Serv., Forest Prod. Lab., Madison, Wis., 1995; WANG et al., Nondestructive methods of evaluating quality of wood in preservative-treated piles, Res. Note FPL-RN-0274, Madison, Wis.: U.S. Department of Agriculture, Forest Service, Forest Products Laboratory, 2000, p. 9; and WANG, X., Stress wave-based nondestructive evaluation (NDE) methods for wood quality of standing trees, Ph.D. Dissertation, Michigan Technological University, Houghton, Mich., 1999; which are all incorporated herein by reference. Additionally, a specific embodiment for determining a $MOE_{SW}$ is provided below.

4. DETERMINING A MODIFIED MOE USING A MODELS

In some embodiments, modules are used to modify or predict a MOE. For example, a regression model may be used to modify a MOE measured by a stress-wave technique to predict what the MOE would be for a static bending technique. An example mathematical linear regression model equation is:

$$y = a + bx \quad (8)$$

where y is the modified MOE, a and b are empirical constants, and x is a measured MOE (e.g., $MOE_T$, $MOE_{SW}$, etc.) by nondestructive evaluation. For example and in one embodiment, the analysis module 110 receives a $MOE_{SW}$ from the one or more input devices 105, and calculates a predictive MOE using the received $MOE_{SW}$ and equation (8). In other embodiments, the analysis module 110 receives one or more physical properties of the log (e.g., the length of a log) and one or more sensed parameters (e.g., $\Delta t$ for a stress wave evaluation) from the one or more input devices 105, and calculates a predictive MOE using equations (6), (7) and (8). The empirical constants may be previously stored within the analysis module 110, and may be based on experimental testing. Specific examples for determining a predictive MOE using a linear regression model are provided below.

Multivariable regression modules can also be used to predict a MOE. An example mathematical multivariable regression model is:

$$y = a x_1^b x_2^c \quad (9)$$

where y is the predicted MOE; a, b and c are empirical constants; $x_1$, is a nondestructive MOE (e.g., $MOE_T$, $MOE_{SW}$, etc.); and $x_2$ is a physical property of the log (e.g., a diameter-to-length ration). For example and in one embodiment, the analysis module 110 receives a $MOE_{SW}$ from the one or more input devices 105, and calculates a predictive MOE using the received $MOE_{SW}$ and equation (9). In other embodiments, the analysis module 110 receives one or more physical properties of the log (e.g., the diameter of a log) and one or more sensed parameters (e.g., Δt for a stress wave evaluation) from the one or more input devices 105, and calculates the predictive MOE using equations (6), (7) and (8). The empirical constants may be previously stored within the analysis module 110, and may be based on experimental testing. Specific examples for determining a predictive MOE using a multi-variable regression model are provided below.

While two equations for determining a predictive MOE was provided, it is envisioned that other equations or relationships may be used to predict a MOE.

5. DETERMINING A FLEXURAL STIFFNESS

Of the properties and parameters that can be measured nondestructively, e.g., density, appearance, MOE, and stiffness, etc., stiffness is used most frequently to predict the strength of wood materials. Flexural stiffness (EI) is expressed as the product of the moment of inertia (I) and modulus of elasticity (MOE) in bending. For logs, the moment of inertia is given by $$I = \frac{\pi d^4}{64} \quad (10)$$

where d is the average diameter of a log. Upon obtaining a MOE, the flexural stiffness of a log can be easily calculated. Of course, the analysis module may receive the measured physical properties and the sensed parameters and directly calculate the flexural stiffness.

An example study was performed for comparing various $MOE_S$ and stiffness determinations. A discussion of the study is provided below.

A. Materials and Methods

First, a sample of small-diameter trees were selected from stands and harvested to obtain logs. Physical properties (e.g., diameters, moisture contents, and densities) of the logs were then measured. This was followed by a sequence of nondestructive tests using longitudinal stress wave, transverse vibration, and static bending techniques to obtain various MOEs and EIs of each log. Statistical analyses were then used to examine the relationships between log properties determined by different techniques.

A total of 159 small-diameter logs, including 109 jack pine (*Pinus banksiana*) and 50 red pine (*Pinus resinosa* Aft.), were nondestructively evaluated in this study. These logs came from trees that were grown on the Ottawa National Forest and the Lake Superior State Forest in Northern Michigan.

The jack pine logs used in this study were obtained from an over-age stand of jack pine, which is beginning to show signs of deterioration. Ranger District personnel are able to visually identify four categories of trees in this type of stand: live healthy trees (merchantable live), live trees that are showing signs of being under stress (suspect), trees that are dead but still containing merchantable material (merchant able dead), and dead trees that have deteriorated to the point of having no merchantable material (unmerchantable dead). The forest is treating considerable acreages of these jack pine stands through commercial salvage sales. To be able to properly estimate the value of these stands, better information on the value of each of the four categories of trees is needed. Trees of each of these categories were selected for this study to address this need. The estimated ages of these jack pine trees ranged from 50 to 70 years old. The diameter at breast height (DBH) of sampled trees ranged from 5.0 to 12.2 inches (127 to 310 mm).

Red pine logs were obtained from 38 years old research plots that had stocking level as the main treatment. The objective of the original study is to examine the growth of red pine over time at various stocking levels and correlate volume yield with financial yield at the different initial stocking levels. Plots at five levels of stocking were available 220, 320, 420, 620, and 820 trees per acre. Ten trees were harvested from each of the stocking level plots. The DBH of sampled trees ranged from 4.70 to 11.50 inches (119 to 292 mm).

After these sampled trees were harvested, a 16-ft-(4.88-m-) long butt log was bucked from each tree on site and then transported to the Forestry Sciences Lab, USDA Forest Service, North Central Research Station in Houghton, Mich. for various nondestructive testing. Upon arrival at the Forestry Sciences Lab, a 2-ft-(0.61-m-) long section from each end of the butt log was then cut off and sent to the Forest Products Laboratory at Madison, Wis. for pulping studies. The remaining 12-ft-(3.66-m-) long logs were then used for the purpose of this study. In order to determine moisture content (MC) of sampled trees, 3 cookies were cut from butt, middle, and top of each tree respectively. Green weight and oven-dry weight of these cookies were then obtained and used to determine tree MC. For each 12-ft-(3.66-m-) long log, the green weight and the diameters of both ends were measured to obtain the green density and the moment of inertia of the log.

Figure 9:
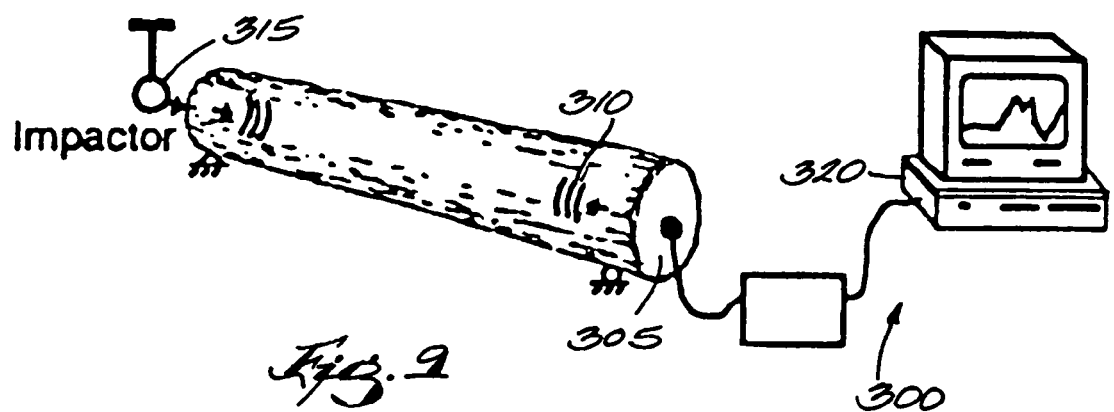
FIG. 9 is a schematic representation of an experimental setup for a stress-wave measurement performed on a log.

Each log was first evaluated using a longitudinal stress wave technique to obtain an estimate of dynamic modulus of elasticity ($MOE_{SW}$) of the log. FIG. 9 shows the experimental setup 300 for the stress wave measurements on the logs. An accelerometer 305 was attached to one end of the log. A stress wave 310 was introduced to the log through a hammer impact 315 on the opposite end, and the resulting stress wave 310 was recorded using a personal computer 320. A detailed description of the instrumentation and analysis procedures can be found in ROSS et al., Technique for nondestructive evaluation of biologically degraded wood, Experimental Tech, 18(5), 1994, pp. 29–32, which is incorporated herein by reference. A discussion of its application to large specimens is included in SCHAD et al., 1995 Stress wave techniques for determining quality of dimensional lumber from switch ties, FPL-RN-0265, USDA Forest Serv., Forest Prod. Lab., Madison, Wis., 1995, which is incorporated herein by reference. From stress wave measurements, the stress wave speed (C) in a log was determined by equation (6). The dynamic modulus of elasticity ($MOE_{SW}$) was then calculated using equation (7).

Figure 10:
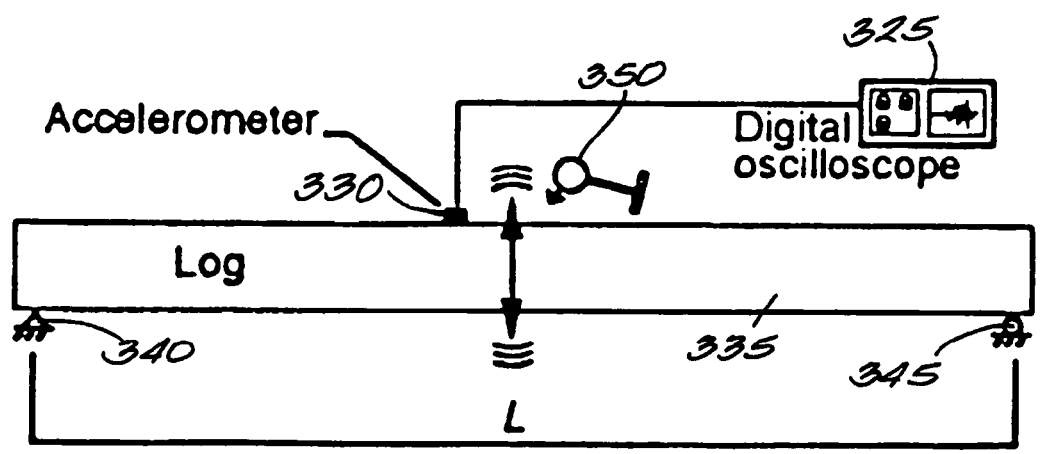
FIG. 10 is a schematic representation of an experimental setup for a transverse-vibration measurement performed on a log.

After stress wave tests, the logs were vibrated using a transverse vibration technique. FIG. 10 shows a schematic representation of the experimental setup used for the transverse vibration measurement. A digital oscilloscope 325 and an accelerometer 330 were used in this test. The log 335 under test was supported at one end by a knife-edge support 340, and at the opposite end, by a point support 345. The accelerometer 330 was located in the middle of the log 335 and glued on the upside surface, where the bark was removed or polished to improve the contact between accelerometer 330 and the log 335. The log 335 was then set into excitation by impacting the middle part of the log using a rubber hammer 350. The free-vibration-response of the log was observed in the oscilloscope 325. Note that the signal observed was a series of pulses with a gradually decreasing (i.e., decaying) amplitude. The vibrational parameter measured was natural frequency. The value for the dynamic modulus of elasticity ($MOE_v$) of the logs was calculated with equation (5).

Static bending tests were then performed on the logs to obtain the flexural stiffness (EI) and static modulus of elasticity ($MOE_s$) of the logs. Measuring MOE of a member by static bending techniques has been widely considered as the foundation of lumber grading and NDE of wood and wood-based materials. However, this technique is rarely used to evaluate the MOE of logs as a standard method. Consequently no standard testing procedure exists for testing small-diameter logs. Even though, we assume the $MOE_s$ of logs to be the real MOE for logs, and used the $MOE_s$ to evaluate the dynamic modulus of elasticity of logs determined by stress wave and transverse vibration techniques.

Figure 11A:
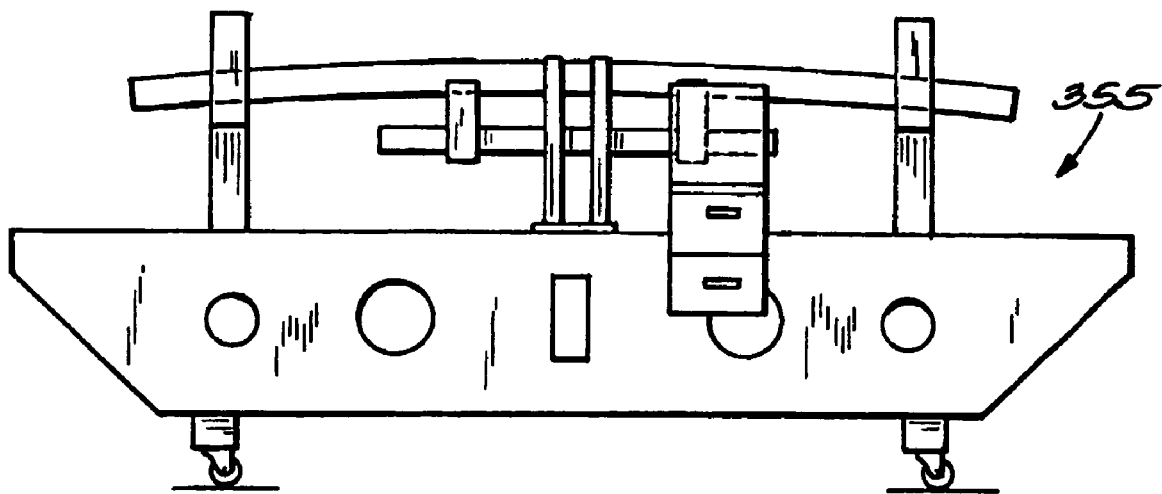
FIG. 11 is a front view of an experimental setup for a static-bending measurement performed on a log.
Figure 11B:
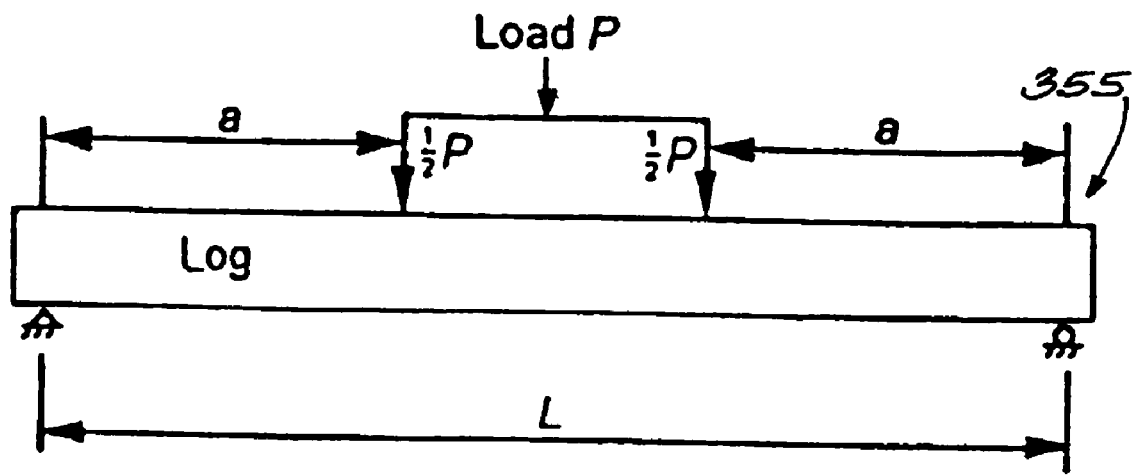
Figure 16:
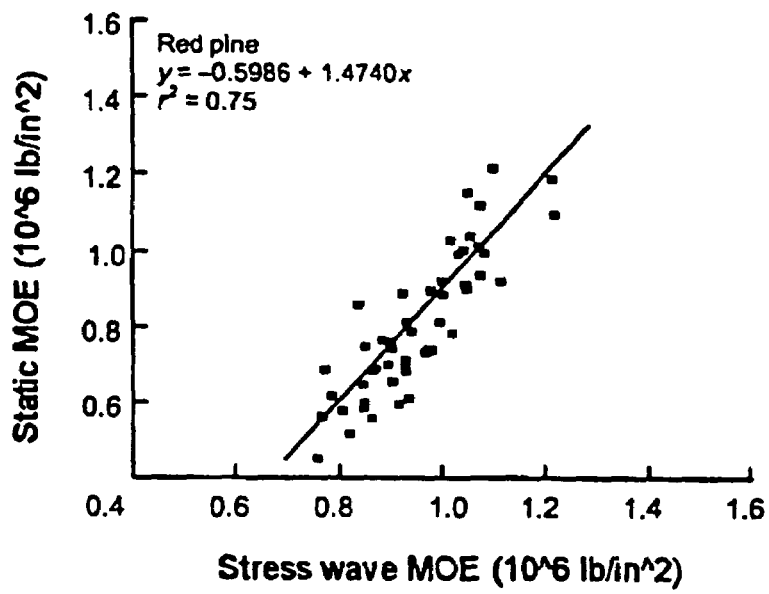
FIG. 16 is a graph representing the relationships of stress-wave MOE to static MOE for red pine logs.
Figure 17:
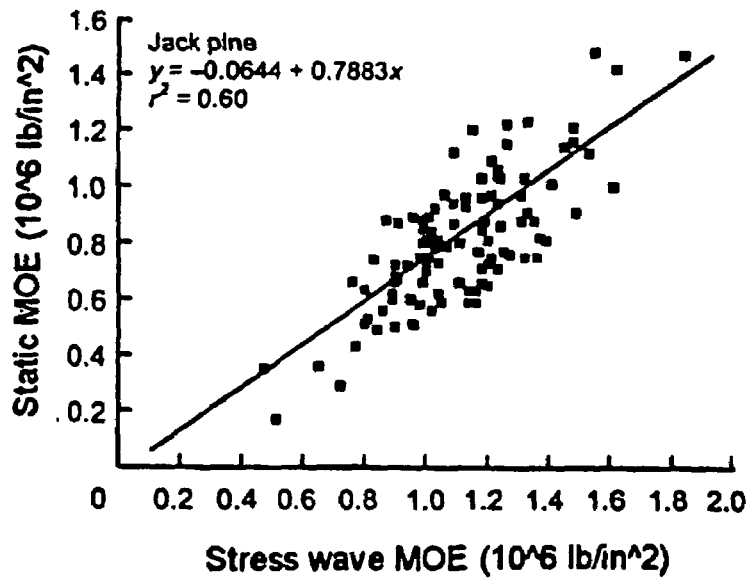
FIG. 17 is a graph representing the relationships of stress-wave MOE to static MOE for jack pine logs.
Figure 18:
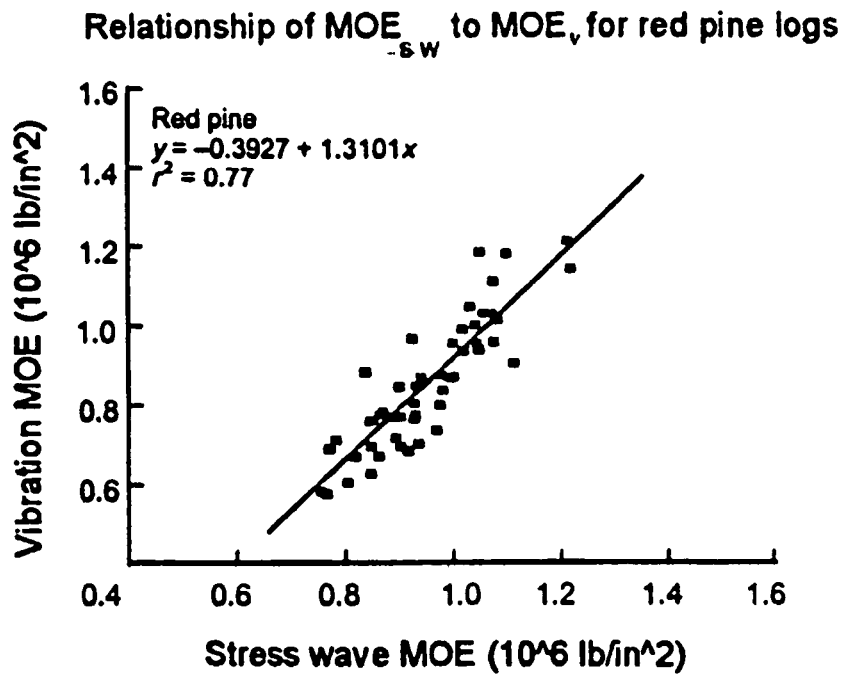
FIG. 18 is a graph representing the relationships of stress-wave MOE to vibration MOE for red pine logs.
Figure 19:
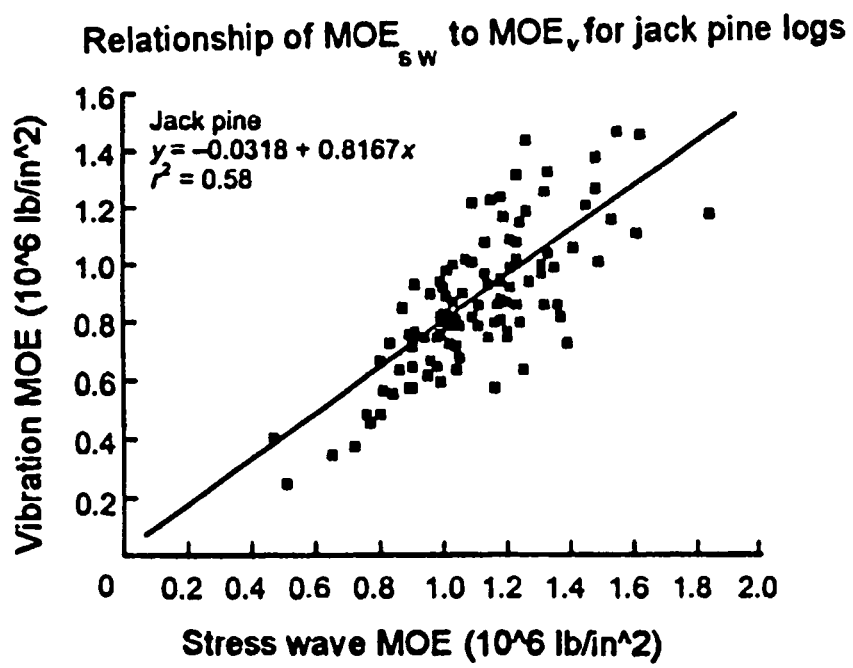
FIG. 19 is a graph representing the relationships of stress-wave MOE to vibration MOE for jack pine logs.

A Metriguard Model 312 Bending Proof Tester 355 (FIG. 11a) was used to conduct static bending tests on all logs. FIG. 11b shows the general bending configuration used. The testing machine was originally designed for proof-loading dimensional lumber. In order to test logs, we modified the two end-supports to fit to the geometrical shape of small-diameter logs. The modified supports allow testing logs with a maximum diameter of 12 inches (305 mm). The span between two supports was set as 115.5 inches (2.93 m). The distance from loading point to the nearest support was 38.5 inches (0.98 m), one third of the span. A load was applied to the log through two bearing blocks. Deflection was measured in the central region, a zone of pure bending without shear deformation. The log under test was first pre-loaded to 100 lbs (445 N) and the deflection was set to zero. This procedure was mainly used to improve the contact between log, supporters, and bearing blocks and eliminate the effect of bark on the deflection measurement. The log was then loaded to 0.2 inches (5.08 mm) deflection. The practical load value corresponding to this deflection was then recorded. The static modulus of elasticity ($MOE_S$) of the log was then calculated using equation (2).

B. Results and Discussion i. Physical Characteristics

Table 1 (FIG. 12) summarizes the various physical characteristics of the red pine and jack pine logs. The average diameters of the butt logs obtained from the trees ranged from 4.4 to 10.2 inches (112 to 259 mm) for red pine and from 4.67 to 10.99 inches (119 to 279 mm) for jack pine. This is a typical diameter range of small-diameter timber. For both species, the average moisture content exceeded the fiber saturation point (about 30%). However, red pine logs apparently have a much higher MC level than jack pine logs. The individual values ranged from 88.2 to 144.6 percent for red pine logs and from 31.2 to 65.0 percent for jack pine logs. The low MC level for jack pine logs was caused by their particular tree source which included live, suspect, and dead trees. The suspect and dead trees had already lost a lot of moisture by the time they were harvested. Therefore, the moisture content of some logs obtained from dead trees was close to or even lower than the fiber saturation point.

It was also noted that red pine logs have higher density than jack pine logs. The density values for red pine logs ranged from 48.0 to 56.5 pcf (0.77 to 0.90 g/cm$^3$), and those for jack pine logs ranged from 28.66 to 53.73 pcf (0.46 to 0.86 g/cm$^3$). The lower value and large range of density for jack pine logs was also due to their particular tree source.

In appearance, jack pine logs show differences from red pine logs in terms of stem shape in cross section and straightness of logs. Red pine logs are mostly round-shaped and very straight. Whereas some jack pine logs have more irregular shape (not round in cross section) and curved stem, which could introduce errors in the determination of density and moment of inertia of these logs.

ii. MOE of Logs

Results obtained from various NDE measurements of both red pine and jack pine logs are summarized in Table 2 (FIG. 13). The basic statistics of dynamic MOE (determined by the stress wave and transverse vibration techniques) and static MOE (determined by the static bending technique within elastic region) for both species were given in this table.

The static MOE ($MOE_s$) of logs ranged from 0.45 to 1.21 $\times 10^6$ lb/in$^2$ (3.10 to 8.34 GPa) with a mean value of $0.80 \times 10^6$ lb/in$^2$ (5.52 GPa) for red pine and the range for jack pine logs was 0.17 to $1.48 \times 10^6$ lb/in$^2$ (1.17 to 10.20 GPa) with a mean value of $0.81 \times 10^6$ lb/in$^2$ (5.58 GPa). It was found that the stress wave technique produced a higher estimate of MOE for both species. For red pine logs, the mean $MOE_{SW}$ is 11.8% and 18.8% greater than its vibrational and static counterpart respectively. For jack pine logs, the mean $MOE_{SW}$ is 21.6% and 24.7% greater than its vibrational and static counterpart. We believe that the higher value of $MOE_{SW}$ could be related with the wave propagation mechanism, dimension of logs, and the moisture state of wood in logs.

The stress waves traveled faster in the outer portion of the wood (i.e., the mature wood) when it was propagated through a log in the longitudinal direction. This led to a higher stress wave speed on a log and increased the value of the $MOE_{sw}$, which in turn overestimated the $MOE_{sw}$ of the log. It was also found that the diameter-to-length ratio could be a critical factor that may affect the stress wave behavior in logs. Quantitative analyses of the overestimation in $MOE_{sw}$ of logs have not been reported.

Compared with the $MOE_{SW}$ of logs, the dynamic MOE of logs determined from the transverse vibration technique ($MOE_v$) is much closer to static MOE of logs. The $MOE_v$ of red pine logs ranged from 0.58 to $1.22 \times 10^6$ lb/in$^2$ (4.00 to 8.40 GPa) and the range for jack pine logs was 0.25 to $1.47 \times 10^6$ lb/in$^2$ (1.72 to 10.14 GPa). The mean value of $MOE_v$ of logs was about 7 percent greater than the mean $MOE_s$ of logs for both species.

iii. MOE Relationships.

Statistical analysis procedures were used to examine the relationships between the various MOE of red pine and jack pine logs. The results obtained from regression analyses are presented in Table 3 (FIG. 14) and Table 4 (FIG. 15).

a. Univiarable Regression Models

The correlations among various MOE could be represented by linear regression models (y=a+bx). The results of the comparison between three different techniques are reported in terms of correlation coefficients that reflect the possible reliability of the method for prediction purposes. The square of the correlation coefficient expresses the percentage of the total variability explained by the regression line.

In general, the dynamic MOE ($MOE_{SW}$ and $MOE_V$) of logs was very closely correlated with the static MOE ($MOE_S$) for both red pine and jack pine logs. The correlation coefficients were found to be 0.87 ($MOE_{SW}$ vs. $MOE_S$) and 0.97 ($MOE_V$ and $MOE_S$) for red pine logs. Those for jack pine logs were 0.77 ($MOE_{SW}$ vs. $MOE_S$) and 0.92. The linear regression analyses indicated that the developed regression models were statistically significant at the 0.01 confidence level.

FIGS. 16, 17, 18 and 19 show the relationships of dynamic MOE, predicted by stress wave technique, to dynamic MOE predicted by transverse vibration technique and static bending MOE for both species. It was apparent that the red pine logs produced a better correlation (r=0.87–0.88) than the jack pine logs (r=0.76–0.77). This could be attributed to the geometrical differences between two species. It was evident that irregular shape (not round in cross section and curved in stem) of some jack pine logs could introduce errors in diameter measurements, thus cause errors in the density and the MOE determinations, especially in the $MOE_{SW}$ determinations.

It was also noted that the plotted data points were more heavily concentrated below the 45° line than above, thus indicating that stress wave technique yields higher MOE values than its vibrational and static counterpart. As was discussed earlier, the higher value of $MOE_{SW}$ could be caused by several factors such as wave propagation mechanism, log size, and moisture state of wood. Of these factors, log size (diameter D and length L) seems more important because it could affect stress wave behavior in logs. A high diameter-to-length ratio (D/L) could cause significant changes in wave propagation path with respect to longitudinal direction when applying longitudinal stress wave measurements on logs. Therefore, it seems that the effect of log size should not be neglected in the MOE regression models.

Figure 21:
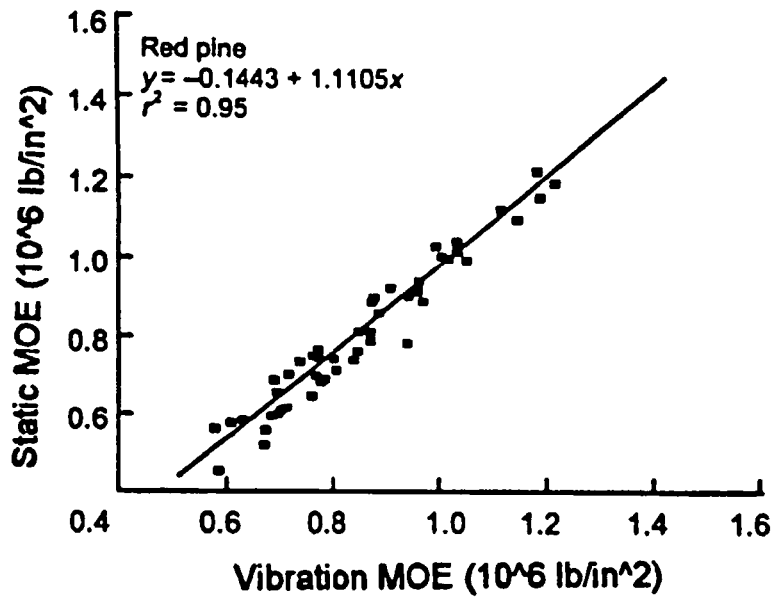
FIG. 21 is a graph representing the relationships of vibration MOE to static MOE for jack pine logs.
Figure 20:
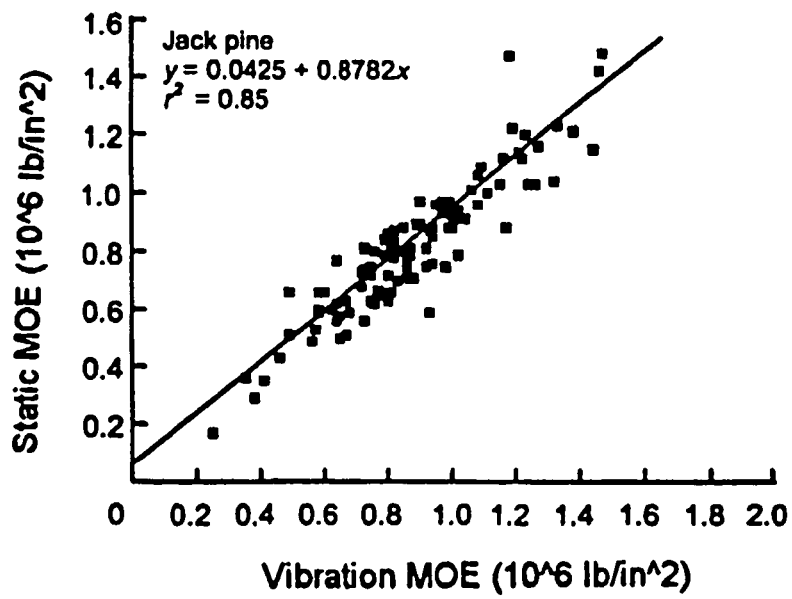
FIG. 20 is a graph representing the relationships of vibration MOE to static MOE for red pine logs.

The relationships between $MOE_V$ and $MOE_S$ of red pine and jack pine logs are shown in FIGS. 20 and 21. The results from transverse vibration tests demonstrated that a significant improvement had been achieved in comparison to the results from stress wave tests. In regard to the relationship of $MOE_V$ to $MOE_S$, it was found that two species could be combined and represented as a single population. The correlation coefficient relating the $MOE_V$ to $MOE_S$ was 0.93. This value indicates clearly that the variation caused by these two species does not affect the relationship.

b. Multi-variable Regression Models

In regard to stress wave MOE ($MOE_{SW}$), it was found that the univariable linear regression models resulted in a correlation coefficient of 0.77–0.87 with static bending MOE. This value, although significant, indicates a greater scatter of points about the regression line than had occurred in $MOE_V$. In an effort to obtain a better prediction model for modulus of elasticity of logs, a multi-variable regression model relating the static MOE ($MOE_{SW}$) to the stress wave MOE ($MOE_{SW}$) and the diameter-to-length ratio was developed. The mathematical regression models used in this analysis were assumed to be of the form shown in equation (9).

The MOE of logs predicted by this equation was then compared against the static bending $MOE_S$ of logs. Results of the regression analyses and values for the constants in the equations are summarized in Table 4 (FIG. 15).

Figure 22:
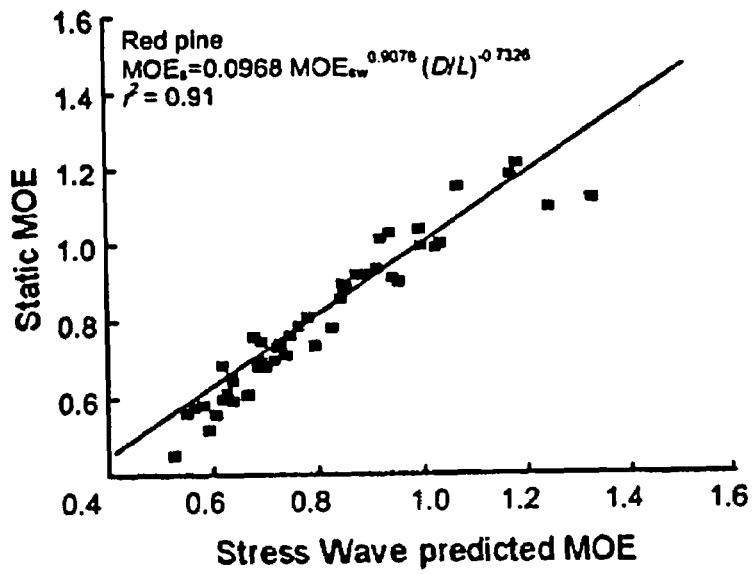
FIG. 22 is a graph representing the relationships of predictive stress-wave MOE to static MOE for red pine logs.
Figure 23:
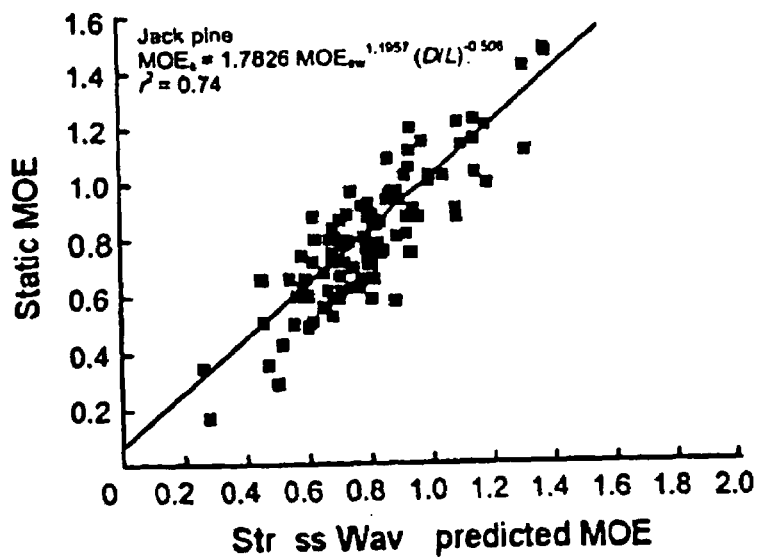
FIG. 23 is a graph representing the relationships of predictive stress-wave MOE to static MOE for jack pine logs.

The relationship between stress-wave-predicted MOE using the developed multi-variable model and the static MOE of logs are shown in FIGS. 22 and 23. They indicate that a strong relationship exists between stress-wave-predicted MOE and static MOE. Compared with the univariable linear regression model, a significant improvement was achieved in the multi-variable models. The correlation coefficient r increased from 0.87 (red pine) and 0.77 (jack pine) for the univariable model to 0.95 (red pine) and 0.86 (jack pine) for the multi-variable model. This showed that the diameter-to-length ratio (D/L) had an interactive effect that contributed significantly when used in conjunction with $MOE_{SW}$.

iv. Flexural Stiffness Relationships.

Of the parameters that can be measured nondestructively, e.g., density, appearance, MOE, and stiffness, etc., stiffness is used most frequently to predict the strength of wood materials. Therefore, it is important to know the relationships between the stiffness determined by these three techniques.

Flexural stiffness is expressed as the product of the moment of inertia (I) and modulus of elasticity (MOE) in bending. For logs, the moment of inertia is given by equation (10). Knowing the modulus of elasticity of logs determined by these techniques, the various flexural stiffness of logs can be easily calculated.

Figure 25:
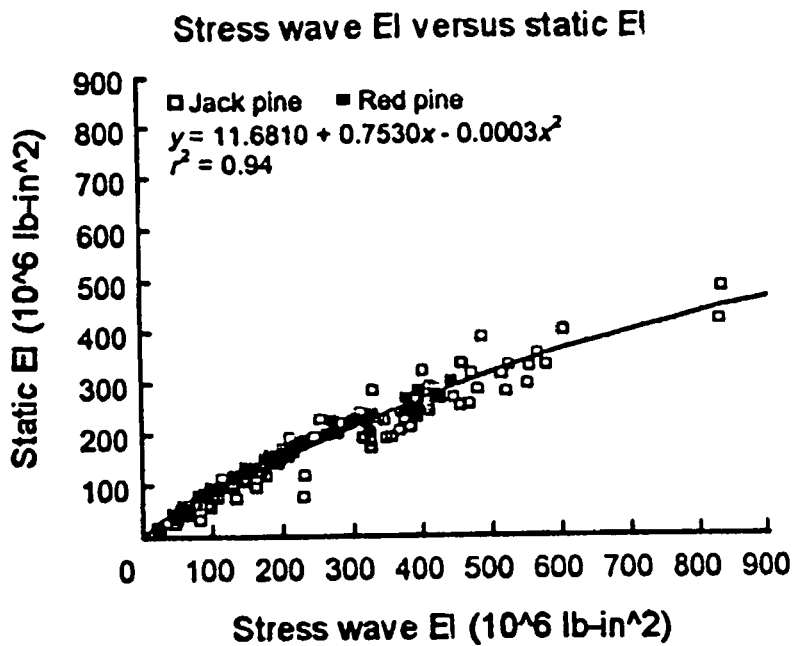
FIG. 25 is a graph representing the relationships of stress-wave EI to static EI.
Figure 26:
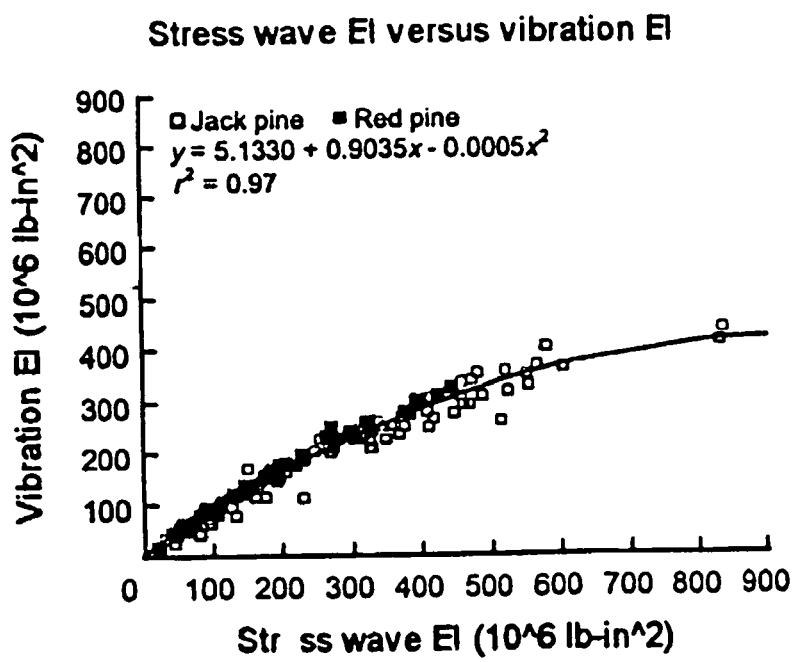
FIG. 26 is a graph representing the relationships of stress-wave EI to vibration EI.
Figure 22:
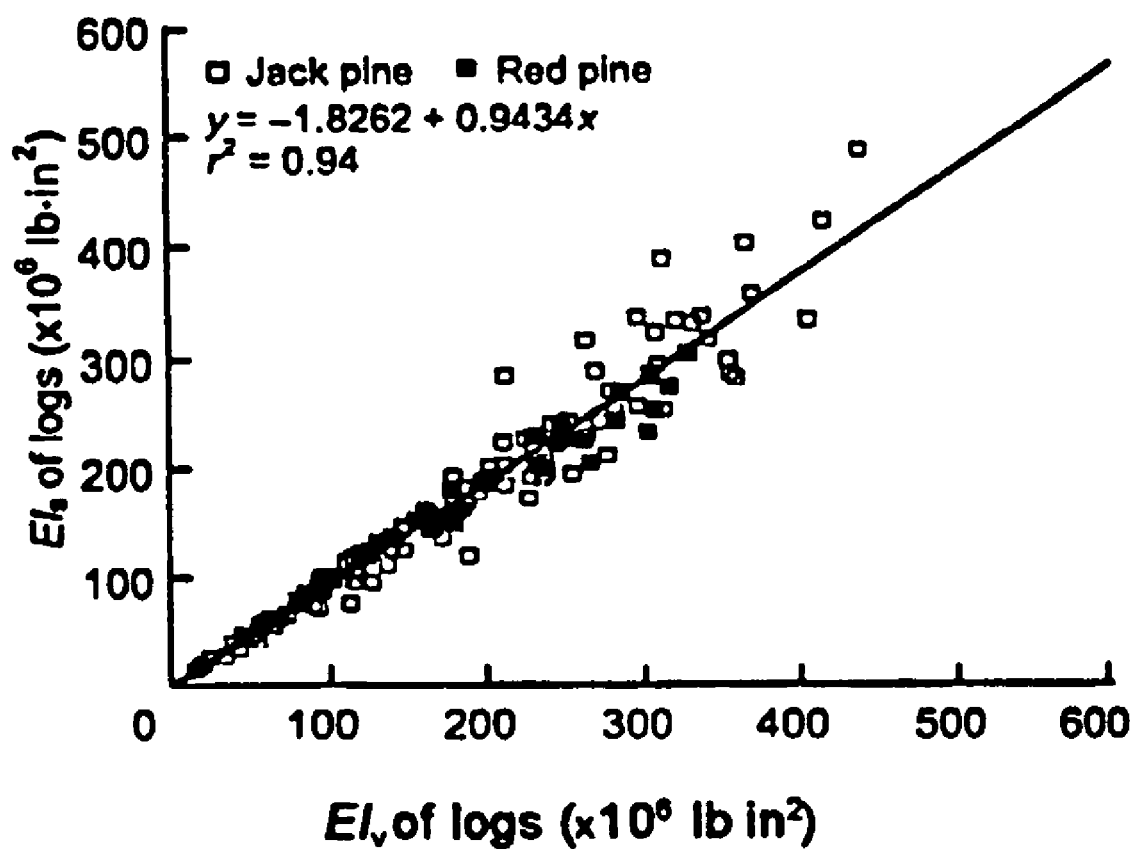

The relationships between various log stiffness (stress wave EI, vibration EI, and static EI) are shown in Table 5 (FIG. 24) and FIGS. 25, 26 and 27. It was recognized that red pine and jack pine logs show no distinction in regard to the stiffness relationship. Therefore, we combined these two species together and treated them as a single population.

The results revealed that the correlations between these nondestructively determined stiffness were extraordinarily strong. In FIGS. 25 and 26, the stiffness from transverse vibration and static bending tests were plotted as a function of stress-wave-determined stiffness. It is important to note that, compared with the MOE relationships, the correlations between stress wave technique and the transverse vibration and static bending techniques have been improved significantly in term of flexural stiffness. Regression analyses indicate that a second-order polynomial regression model ($y=a+bx+cx^2$) could best fit the experimental data. The correlation coefficients were 0.97 (stress wave EI vs. vibration EI) and 0.94 (stress wave EI vs. static EI) respectively. The developed regression models accounted for 97 and 94 percent of observed behavior.

FIG. 27 shows the comparison between transverse vibration and static bending techniques in term of flexural stiffness of logs. Just as in the case of the MOE relationship, a linear regression model was found to be the best fitting function to the experimental data. The correlation coefficient was 0.94, indicating that 94 percent of observed behavior has been accounted for.

C. Conclusion

Based on the results of these experiments, it can be concluded that small-diameter red pine and jack pine logs can be successfully evaluated by longitudinal stress wave, transverse vibration, or static bending techniques. The dynamic MOE ($MOE_{SW}$ and $MOE_V$) of logs was found to be well-correlated with the static MOE for both species.

Further, it was found that the a physical parameter (e.g., a diameter-to-length ratio (D/L)) had an interactive effect that contributed significantly when used in conjunction with measured parameters (e.g., a $MOE_{SW}$). For example, the developed multi-variable model relating static MOE ($MOE_S$) to stress wave MOE ($MOE_{SW}$) and diameter-to-length ratio (D/L) was found to be a better predictor for static modulus of elasticity of logs. Red pine and jack pine logs therefore could be combined and represented as a single population in the prediction model.

Extraordinarily strong relationships were found between various nondestructively determined log stiffness. Compared with the MOE relationships, the correlations between the stress wave technique and the transverse vibration and static bending techniques were improved significantly in term of flexural stiffness.

Thus, the invention provides, among other things, a new and useful system for and method of performing nondestructive evaluation techniques on a log or round timber. Various features and advantages of the invention are set forth in the following claims.

What is claimed is:

1. A method of evaluating a timber comprising the acts of:
   determining a multi-variable regression model relating a modified modulus of elasticity (MOE) of the timber to at least two variables including a measured MOE of the timber determined by a non-destructive evaluation technique and a physical property of the timber, wherein the physical property can be determined without applying a force to the timber;
   determining the measured MOE of the timber by the non-destructive evaluation technique;
   determining the physical property of the timber; and
   calculating the modified MOE of the timber based at least in part on using the measured MOE and the determined physical property of the timber in the multi-variable regression model.

2. A method as set forth in claim 1 wherein the non-destructive evaluation technique is a stress wave propagation technique.

3. A method as set forth in claim 2 wherein the stress wave propagation technique includes the acts of:
   attaching a sensor to the timber;
   introducing a stress to the timber that results in a stress wave having pulses;
   measuring a time between two consecutive pulses of the stress wave;
   calculating the speed of the stress wave based at least in part on the measured time; and
   calculating the measured MOE based at least in part on the calculated speed of the stress wave.

4. A method as set forth in claim 1 wherein the physical property includes a diameter and a length, and the act of a determining the physical property of the timber includes the acts of measuring a diameter of the timber and measuring a length of the timber,
   wherein the act of calculating the modified MOE includes the act of calculating the modified MOE based at least in part on the measured MOE, the measured diameter and the measured length.

5. A method as set forth in claim 1 wherein the timber is a log.

6. A method as set forth in claim 1 wherein the physical parameter is a diameter and the act of determining the physical property of the timber includes the act of measuring a diameter of the timber.

7. A method of evaluating a timber comprising the acts of:
   determining a measured modulus of elasticity (MOE) of the timber;
   measuring a property of the timber; and
   calculating a modified MOE of the timber based in part on the measured MOE and the measured property, wherein the act of measuring the property includes measuring a diameter of the timber (n) times, and wherein the act of calculating the modified MOE includes the acts of determining an average diameter of the timber based on the (n) measurements and calculating the modified MOE based at least in part on the measured MOE and the average diameter.

8. A method of evaluating a timber comprising the acts of:
   determining a measured modulus of elasticity (MOE) of the timber;
   measuring a property of the timber; and
   calculating a modified MOE of the timber based in part on the measured MOE and the measured property, wherein the act of measuring the property includes the acts of measuring a diameter of the timber and measuring a length of the timber, wherein the act of calculating the modified MOE includes the act of determining a diameter-to-length ratio of the timber based at least in part on the measured diameter and the measured length, and calculating the modified MOE based at least in part on the measured MOE and the diameter-to-length ratio.

9. A method as set forth in claim 8 wherein the act of calculating the modified MOE includes the act of calculating the modified MOE using the formula $$y = a x_1^b x_2^c,$$

where y is the modified MOE, $x_1$ is the measured MOE, $x_2$ is the diameter-to-length ratio, and a, b and c are constants.

10. A method as set forth in claim 8 and further comprising the act of calculating a flexural stiffness of the timber based at least in part on the modified MOE.

11. An analysis module as for evaluating a timber comprising:
   at least one input terminal connectable to at least one input device, the at least one input terminal being operable to receive at least one signal representing at least one measured property of the timber, the at least one measured property including a diameter of the timber, and the at least one input terminal being operable to receive at least one determined parameter of the timber determined in response to a stress wave being applied to the timber;
   a processor coupled to the at least one input terminal, the processor determining a predictive modulus of elastic (MOE) of the timber based at least in part on the at least one measured property and the at least one parameter; and
   an out-put terminal coupled to the processor an connectable to an output device, the output terminal being operable to transmit a third signal representing the predictive MOE, wherein the at least one measured property includes a diameter-to-length ratio of the timber, and
   wherein the processor determines the predictive MOE based at least in part on the diameter-to-length ratio of the timber.

12. An analysis module as set forth in claim 11 wherein the at least one determined parameter includes a measured modulus of elasticity (MOE), and
   wherein the processor determines the predictive MOE based at least in part on measured MOE.

13. An analysis module as set forth in claim 12 wherein the measured MOE represents a MOE determined in response to the stress wave being applied to the timber.

14. An analysis module as set forth in claim 11 wherein the at least one determined parameter includes an average time between pulses determined in response to the stress wave being applied to the timber,
   wherein the processor determines the predictive MOE based at least in part on the average time between pulses.

15. An analysis module as set forth in claim 11 wherein the processor further determines a flexural stiffness based at least in part on the at least one measured property and the at least one determined parameter.

16. A method as set forth in claim 11 wherein the timber is a log.

17. A system for evaluating a timber comprising:
an input device operable to accoutre at least one property of the timber, the at least one property including a diameter of the timber, and being further operable to generate a first signal representing the at least one property:
a sensor attachable to the timber, the sensor being operable to sense a stress wave propagating through the timber and to generate a second signal representing at least one parameter of the sensed stress wave;
an analysis module coupled to the input device, the analysis module being operable to receive the first and second signals, to determine a predictive modulus of elasticity (MOE) based at least in part on the first and the second signal and to generate a third signal representing the predictive modulus of elasticity; and
an output device operable to receive the third signal,
wherein the at least one property includes a length of the timber, and
wherein the analysis module determines the predictive MOE based at least in part on a diameter-to-length ratio of the timber.

18. A system as set forth in claim 17
wherein the sensed stress wave includes at least two pulses,
wherein the analysis module is further operable to analyze the sensed stress wave to determine an average time between the pulses, wherein the at least one parameter is an average time between the pulses and
wherein the analysis module determines the predictive MOE based at least in part on the average time between the pulses.

19. A system as set forth in claim 17 wherein the sensed stress wave includes at least two pulses,
wherein the at least one parameter is an average time between the pulses, and
wherein the analysis module determines the predictive MOE based at least in part on the average time between the pulses.

20. A method as set forth in claim 17 wherein the timber is a log.

21. A software program for evaluating a timber, the software program including at least one software module stored in a computer readable medium, the software module beingexecutable to:
receive at least one measured property of the timber including a measured property based on a diameter of the timber,
receive at least one determined parameter of the timber determined in response to a stress wave being applied to the timber,
calculate a predictive modulus of elasticity (MOE) based at least in part on a multi-variable regression model that relates the predictive MOE to at least two variables including the diameter and the determined parameter, wherein the multi-variable regression model is obtained by testing a plurality of timber samples and for each timber sample, determining a corresponding diameter, determining a first MOE value by sensing a stress wave propagating through the timber sample, determining a second MOE value by a second non-destructive evaluation technique, and relating the plurality of first MOE values and diameters to the plurality of second MOE values, and output the predictive modulus of elasticity.

22. A software program as set forth in claim 21 wherein the software module is executable to calculate the predictive MOE by being further executable to
calculate a measured MOE based at least in part on the at least one parameter, and
calculate the predictive MOE using the measured MOE.

23. A method as set forth in claim 21 wherein the timber is a log.

24. A software program for evaluating a timber, the software program including at least one software module stored in a computer readable medium, the software module being executable to:
receive at least one measured property of the timber including a measured property based on a diameter of the timber,
receive at least one determined parameter of the timber determined in response to a stress wave being applied to the timber,
calculate a predictive modulus of elasticity (MOE) based at least in part on the diameter and the determined parameter, and
output the predictive modulus of elasticity, wherein the software module is executable to calculate the predictive MOE by being further executable to
calculate a measured MOE based at least in part on the at least one parameter, and
calculate the predictive MOE using the measured MOE, and
wherein the software module is executable to calculate the predictive MOE by being further executable to calculate the predictive MOE using the formula $$y = ax_1^b x_2^c,$$

where y is the predictive MOE, $x_1$ is the measured MOE, $x_2$ is a diameter-to-length ratio, and a, b and c are constants.

25. A software program for evaluating a timber, the software program including at least one software module stored in a computer readable medium, the software module being executable to:
receive at least one measured property of the timber including a measured property based on a diameter of the timber,
receive at least one determined parameter of the timber determined in response to a stress wave being applied to the timber,
calculate a predictive modulus of elasticity (MOE) based at least in part on the diameter and the determined parameter, and
output the predictive modulus of elasticity, wherein the software module is executable to receive the at least one measured property by being further executable to receive a length of the timber, and
wherein the software module is executable to calculate a predictive MOE by being further executable to calculate the predictive MOE based at least in part on a diameter-to-length ratio of the timber.

26. A software program as set forth in claim 25 wherein the software module is further executable to:
calculate a flexural stiffness of the timber based at least in part on the diameter and the determined parameter; and
output the calculated flexural stiffness.

27. A method for evaluating a timber, the method comprising the acts of:

determining a regression model relating a predictive modulus of elasticity (MOE) of the timber to a measured MOE of the timber determined in response to a stress wave being applied to the timber using a stress wave evaluation technique, wherein the regression model is obtained by testing a plurality of timber samples and for each timber sample, determining a first MOE value by the stress wave evaluation technique and determining a second MOE value by a static bending evaluation technique, and relating the plurality of first MOE values to the plurality of second MOE values, measuring a parameter of the timber determined in response to a stress wave being applied to the timber using the stress wave evaluation technique and calculating the measured MOE of the timber; and calculating a predictive MOE based at least in part on using the measured MOE in the regression model.

28. The method of claim 27, wherein the static bending evaluation technique is a non-destructive technique.

29. A method as set forth in claim 27 wherein the stress wave evaluation technique includes the acts of:

attaching a sensor to the timber;

introducing a stress to the timber that results in a stress wave having pulses;

measuring a time between two consecutive pulses of the stress wave;

and further wherein the act of determining a first MOE value includes the acts of calculating the speed of the stress wave based at least in part on the measured time, and calculating the first MOE value based at least in part on the calculated speed of the stress wave.

30. A method as set forth in claim 27, wherein the regression model is one of a linear regression model, a second-order polynomial regression model, and a multi-variable regression model.

31. A method as set forth in claim 27, wherein the regression model is a multi-variable regression model including as an additional variable a physical property of the timber selected from the group including a diameter, a radius, a length, a diameter-to-length ratio, a cross sectional area, and a volume of the timber.

32. A method as set forth in claim 27, wherein the regression model is a multi-variable regression model including as an additional variable a diameter-to-length ratio of the timber.

33. A method as set forth in claim 27, and further comprising the act of calculating a flexural stiffness of the timber based at least in part on the predictive MOE and a determined moment of inertia of the timber.

* * * * *